(12) United States Patent  
Kawamura et al.

(10) Patent No.: US 8,221,907 B2  
(45) Date of Patent: *Jul. 17, 2012

(54) CHRYSENE DERIVATIVE AND ORGANIC ELECTROLUMINESCENT DEVICE USING THE SAME

(75) Inventors: Masahiro Kawamura, Sodegaura (JP); Kazuki Nishimura, Sodegaura (JP); Toshihiro Iwakuma, Sodegaura (JP); Kenichi Fukuoka, Sodegaura (JP); Chishio Hosokawa, Sodegaura (JP); Masakazu Funahashi, Sodegaura (JP); Tetsuya Inoue, Sodegaura (JP); Yukitoshi Jinde, Sodegaura (JP); Yuichiro Kawamura, Sodegaura (JP); Mitsunori Ito, Sodegaura (JP); Yoriyuki Takashima, Sodegaura (JP); Toshinari Ogiwara, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 274 days.

This patent is subject to a terminal disclaimer.

(21) Appl. No.: 12/666,226

(22) PCT Filed: Jul. 2, 2008

(86) PCT No.: PCT/JP2008/062010  
§ 371 (c)(1),  
(2), (4) Date: Dec. 22, 2009

(87) PCT Pub. No.: WO2009/008311  
PCT Pub. Date: Jan. 15, 2009

(65) Prior Publication Data  
US 2010/0194270 A1 Aug. 5, 2010

(30) Foreign Application Priority Data

Jul. 7, 2007 (JP) ................... 2007-179109  
Jul. 7, 2007 (JP) ................... 2007-179110  
Jul. 7, 2007 (JP) ................... 2007-179111  
Jul. 7, 2007 (JP) ................... 2007-179112  
Jul. 7, 2007 (JP) ................... 2007-179116  
Jul. 7, 2007 (JP) ................... 2007-179122  
Jul. 7, 2007 (JP) ................... 2007-179124  
Apr. 23, 2008 (WO) ............... PCT/JP2008/057837

(51) Int. Cl.  
*H01L 51/54* (2006.01)  
*C07C 13/48* (2006.01)

(52) U.S. Cl. .......... 428/690; 428/917; 585/26; 313/504; 313/506

(58) Field of Classification Search .................. None  
See application file for complete search history.

(56) References Cited

U.S. PATENT DOCUMENTS

2005/0123794 A1* 6/2005 Deaton et al. ............... 428/690  
2006/0134456 A1 6/2006 Ikeda et al.  
2006/0154105 A1 7/2006 Yamamoto et al.  
(Continued)

FOREIGN PATENT DOCUMENTS

JP 2000-273055 A 10/2000  
(Continued)

*Primary Examiner* — Dawn L. Garrett  
(74) *Attorney, Agent, or Firm* — Foley & Lardner LLP

(57) ABSTRACT

A chrysene derivative shown by the following formula:

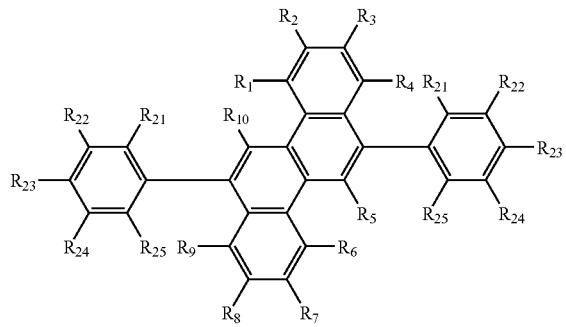

wherein $R_1$ to $R_{10}$ and $R_{21}$ to $R_{25}$ are independently a hydrogen atom, a substituted or unsubstituted alkyl group having 1 to 10 carbon atoms, a substituted or unsubstituted cycloalkyl group having 3 to 10 ring carbon atoms, a substituted or unsubstituted alkylsilyl group having 3 to 20 carbon atoms, a substituted or unsubstituted arylsilyl group having 8 to 30 carbon atoms, or a substituted or unsubstituted aryl group having 6 to 20 ring carbon atoms, provided that at least one of $R_{21}$ to $R_{25}$ is a substituted or unsubstituted fused aromatic ring group having 10 to 20 ring carbon atoms or a substituted or unsubstituted fluorenyl group.

13 Claims, 1 Drawing Sheet

U.S. PATENT DOCUMENTS

| | | |
|---|---|---|
| 2007/0172698 A1 | 7/2007 | Iwakuma et al. |
| 2009/0009066 A1* | 1/2009 | Nishimura et al. ........... 313/504 |
| 2009/0026930 A1* | 1/2009 | Shin et al. ..................... 313/504 |

FOREIGN PATENT DOCUMENTS

| | | |
|---|---|---|
| JP | 2004-002297 A | 1/2004 |
| JP | 2004-075567 A | 3/2004 |
| JP | 2006-052323 A | 2/2006 |
| JP | 2006-052324 A | 2/2006 |
| WO | 2004/016575 A1 | 2/2004 |
| WO | 2005/084083 A1 | 9/2005 |

* cited by examiner

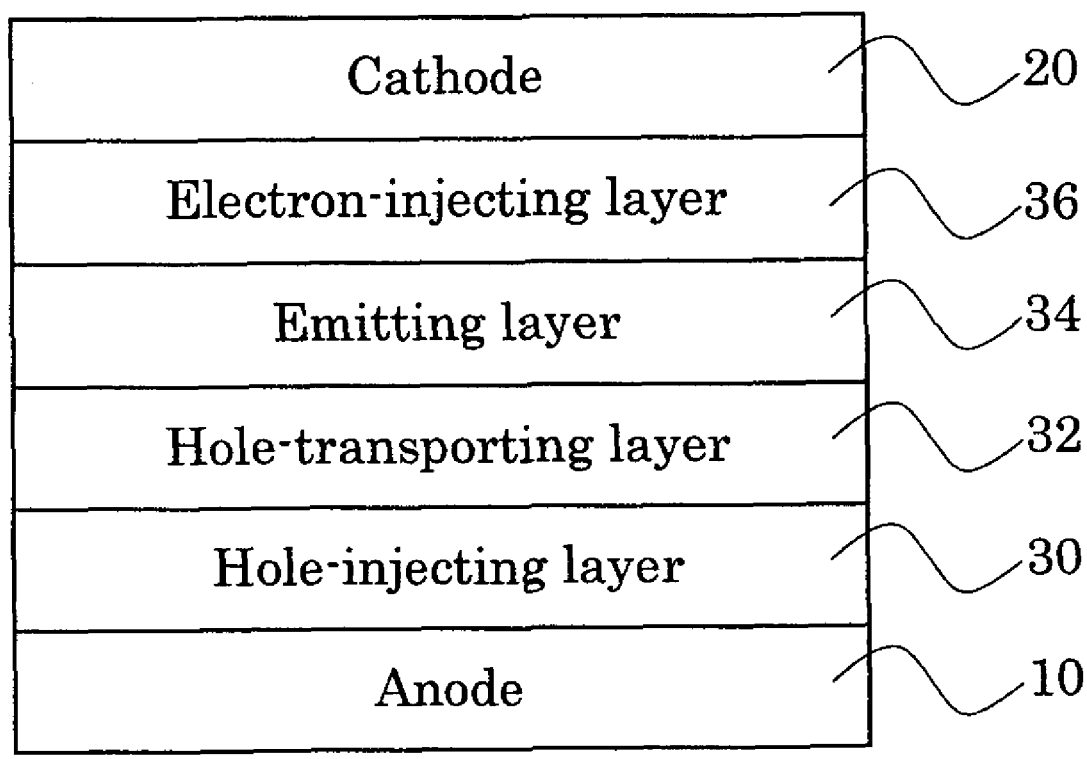

CHRYSENE DERIVATIVE AND ORGANIC ELECTROLUMINESCENT DEVICE USING THE SAME

CROSS REFERENCE TO RELATED APPLICATION

This is the U.S. national phase application under 35 U.S.C. §371 of International Patent Application No. PCT/JP2008/062010, filed Jul. 2, 2008, which claims the benefit of Japanese Applications Nos. 2007-179109, filed Jul. 7, 2007, 2007-179110, filed Jul. 7, 2007, 2007-179111, filed Jul. 7, 2007, 2007-179112, filed Jul. 7, 2007, 2007-179116, filed Jul. 7, 2007, 2007-179122, filed Jul. 7, 2007, 2007-179124, and filed Jul. 7, 2007, and International Patent Application No. PCT/JP2008/057837 filed Apr. 23, 2008. The International Application was published on Jan. 15, 2009 as International Publication No. WO/2009/008311 published in the Japanese language under PCT Article 21(2). The contents of these applications are incorporated by reference herein in their entireties.

TECHNICAL FIELD

The invention relates to a chrysene derivative, which is useful as a material for an organic electroluminescence device and an organic electroluminescence device using the same.

BACKGROUND ART

An organic electroluminescence device (hereinafter the term "electroluminescence" is often abbreviated as "EL") is a self-emission device utilizing the principle that a fluorescent substance emits light by the recombination energy of holes injected from an anode and electrons injected from a cathode when an electric field is impressed.

An organic EL device has attained a remarkable progress. In addition, the organic EL device is expected to be applied to a wide range of applications due to its capability of being driven at a low voltage, a high luminance, variety in emission wavelength, high-speed response, its capability of producing an emitting device which is thin and light in weight, or the like.

Emitting materials used in an organic EL device have been actively studied, since they exert large effects on the color of light emitted by the device and emission life.

Examples of the emission materials include chelate complexes such as tris(8-quinolinolate)aluminum complexes, cumarin derivatives, tetraphenylbutadiene derivatives, bis-styrylarylene derivatives and oxadiazole derivatives. Due to these emitting materials, emission in a visible range from blue to red can be obtained.

In addition, studies have been made on the use of a phosphorescence compound and the use of triplet energy in emission. For example, it is known that an organic EL device using an iridium complex as an emitting material shows a high degree of luminous efficiency.

Patent Documents 1 to 4 each disclose an organic EL device using a chrysene derivative. By using the materials disclosed in these patent documents, the luminous efficiency and lifetime of an organic EL device can be improved. However, further improvements in efficiency and prolongation of lifetime have been required.

Patent Document 1: WO2004/016575
Patent Document 2: JP-A-2000-273055
Patent Document 3: JP-A-2006-52323
Patent Document 4: JP-A-2006-52324

The object of the invention is to provide an organic material which is preferable as a material for an organic EL device. In particular, the invention is aimed at providing a material, as a material for a phosphorescent organic EL device, which has a high efficiency and a long lifetime.

DISCLOSURE OF THE INVENTION

The invention provides the following chrysene derivative.
1. A chrysene derivative shown by the following formula (I):

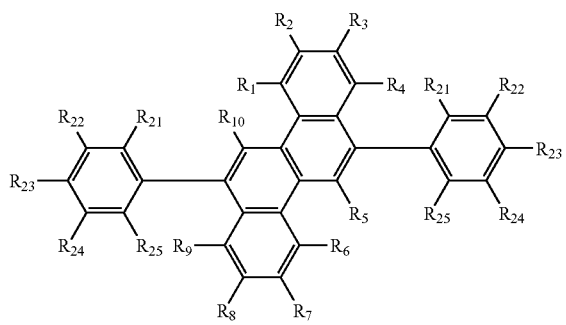

wherein $R_1$ to $R_{10}$ and $R_{21}$ to $R_{25}$ are independently a hydrogen atom, a substituted or unsubstituted alkyl group having 1 to 10 carbon atoms, a substituted or unsubstituted cycloalkyl group having 3 to 10 carbon atoms that form a ring (hereinafter referred to as a ring carbon atom), a substituted or unsubstituted alkylsilyl group having 3 to 20 carbon atoms, a substituted or unsubstituted arylsilyl group having 8 to 30 carbon atoms, or a substituted or unsubstituted aryl group having 6 to 20 ring carbon atoms, provided that at least one of $R_{21}$ to $R_{25}$ is a substituted or unsubstituted fused aromatic ring having 10 to 20 ring carbon atoms or a substituted or unsubstituted fluorenyl group.

2. The chrysene derivative according to 1, wherein $R_1$ to $R_{10}$ are a hydrogen atom.

3. The chrysene derivative according to 1 or 2, wherein one of $R_{21}$ to $R_{25}$ is a substituted or unsubstituted fused aromatic ring having 10 to 20 ring carbon atoms and the rest is a hydrogen atom.

4. The chrysene derivative according to 1 or 2, wherein one of $R_{21}$ to $R_{25}$ is a substituted or unsubstituted naphthyl group or a substituted or unsubstituted phenanthryl group and the rest is a hydrogen atom.

5. A material for an organic electroluminescence device comprising the chrysene derivative according to one of 1 to 4.

6. The material for an organic electroluminescence device according to 5 which is an emitting material.

7. An organic electroluminescence device comprising an anode, a cathode and one or more organic thin film layers including an emitting layer disposed between the anode and the cathode, wherein at least one of the organic thin film layers comprises the material for an organic electroluminescence device according to 5.

8. The organic electroluminescence device according to 7, wherein the emitting layer comprises the material for an organic electroluminescence device.

9. The organic electroluminescence device according to 8, wherein the material for an organic electroluminescence device is a host material.

10. The organic electroluminescence device according to one of 7 to 9, wherein the emitting layer further comprises at least one of a fluorescent dopant and a phosphorescent dopant.

11. The organic electroluminescence device according to 10, wherein the phosphorescent dopant is a metal complex comprising at least one metal selected from the group of Ir, Pt, Os, Au, Cu, Re and Ru and a ligand.

12. The organic electroluminescence device according to 10 or 11, wherein the phosphorescent dopant exhibits an emission spectrum having a maximum peak wavelength at 520 nm to 700 nm.

The invention can provide a chrysene derivative which is preferable as a material for an organic EL device.

The organic EL device utilizing the chrysene derivative of the invention has a long lifetime and a high efficiency, and is capable of driving at a lower voltage.

BRIEF DESCRIPTION OF THE DRAWINGS

FIG. 1 is a schematic cross-sectional view of an organic EL device according to one embodiment of the invention.

BEST MODE FOR CARRYING OUT THE INVENTION

The inventors noticed a chrysene derivative as a material for an organic EL device and made intensive studies. As a result, the inventors have found that a chrysene derivative having a prescribed structure is effective for prolonging lifetime, improving efficiency and lowering voltage of an organic EL device. The invention has been made based on this finding.

The chrysene derivative of the invention is shown by the following formula (1):

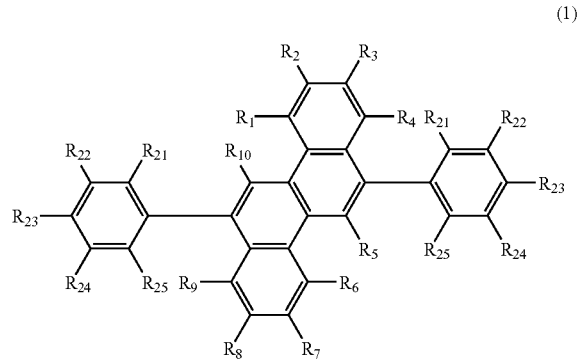

(1)

In the formula (1), $R_1$ to $R_{10}$ and $R_{21}$ to $R_{25}$ are independently a hydrogen atom, a substituted or unsubstituted alkyl group having 1 to 10 carbon atoms, a substituted or unsubstituted cycloalkyl group having 3 to 10 ring carbon atoms, a substituted or unsubstituted alkylsilyl group having 3 to 20 carbon atoms, a substituted or unsubstituted arylsilyl group having 8 to 30 carbon atoms, or a substituted or unsubstituted aryl group having 6 to 20 ring carbon atoms.

However, at least one of $R_{21}$ to $R_{25}$ is a substituted or unsubstituted fused aromatic ring having 10 to 20 ring carbon atoms or a substituted or unsubstituted fluorenyl group.

Examples of the alkyl group having 1 to 10 carbon atoms include methyl, ethyl, n-propyl, isopropyl, n-butyl, sec-butyl, t-butyl, n-octyl, n-decyl and n-hexadecyl. An alkyl group having 1 to 4 carbon atoms is preferable, with a methyl group, an ethyl group and a t-butyl group being further preferable.

Examples of the cycloalkyl group having 3 to 10 carbon atoms include cyclopropyl, cyclobutyl, cyclopentyl, cyclohexyl, cycloheptyl and cyclodecyl. A cycloalkyl group having 3 to 6 carbon atoms is preferable, with a cyclopentyl group and a cyclohexyl group being further preferable.

Examples of the alkylsilyl group having 3 to 20 carbon atoms include a trimethylsilyl group, a triethylsilyl group, a tripropylsilyl group, a tributylsilyl group, a tripentylsilyl group, a tricyclopentylsilyl group, a trihexylsilyl group, a tricyclohexylsilyl group and a diphenylmethylsilyl group. An alkylsilyl group having 3 to 10 carbon atoms is preferable, with a trimethylsilyl group and a triethylsilyl group being further preferable.

Examples of the substituted or unsubstituted arylsilyl group having 8 to 30 carbon atoms include a dimethylsilyl group, a triphenylsilyl group and a trinaphthylsilyl group. An arylsilyl group having 18 to 30 carbon atoms is preferable, with a triphenylsilyl group being further preferable.

Examples of the substituted or unsubstituted aryl group having 6 to 20 ring carbon atoms include phenyl, 1-naphthyl, 2-naphthyl, 1-fluorenyl, 2-fluorenyl, 3-fluorenyl, 4-fluorenyl, 9-fluorenyl, 1-anthryl, 2-anthryl, 9-anthryl, 1-phenanthryl, 2-phenanthryl, 3-phenanthryl, 4-phenanthryl, 9-phenanthryl, 1-naphthacenyl, 2-naphthacenyl, 9-naphthacenyl, 1-pyrenyl, 2-pyrenyl, 4-pyrenyl, 2-biphenylyl, 3-biphenylyl, 4-biphenylyl, p-terphenyl-4-yl, p-terphenyl-3-yl, p-terphenyl-2-yl, m-terphenyl-4-yl, m-terphenyl-3-yl, m-terphenyl-2-yl, o-tolyl, m-tolyl, p-tolyl, p-t-butylphenyl, p-(2-phenylpropyl)phenyl, 3-methyl-2-naphthyl, 4-methyl-1-naphthyl, 4-methyl-1-anthryl, 4'-methylbiphenylyl, 4"-t-butyl-p-terphenyl-4-yl, benzphenanthryl, triphenylenyl, benzanthranyl and chrysenyl. Preferred examples include phenyl, naphthyl, phenathrenyl, triphenylenyl and benzphenanthryl.

Preferably, $R_{21}$ to $R_{25}$ are independently a hydrogen atom or a substituted or unsubstituted aryl group having 6 to 20 ring carbon atoms. Examples of the aryl group include a phenyl group, a fluorenyl group and a fused aromatic ring group having 10 to 20 ring carbon atoms. As the aryl group, for example, one in which 2 to 4 benzene rings are bonded or fused, or the like, can be given.

As the fused aromatic ring having 10 to 20 ring carbon atoms, for example, one in which 2 to 4 benzene rings are fused or the like, can be given.

Examples of the substituents of the alkyl group, the cycloalkyl group, the alkylsilyl group, the arylsilyl group, the aryl group, the fused aromatic ring group and the fluorenyl group include a substituted or unsubstituted aryl group (preferably, an aryl group having 6 to 30 ring carbon atoms, more preferably 6 to 15 ring carbon atoms, the examples of which include a phenyl group, a naphthyl group, a phenanthryl group, a 9,9-dimethylfluorene-2-yl group), an alkyl group and a cyloalkyl group (preferably, an alkyl group or a cycloalkyl group having 1 to 20 carbon atoms, more preferably 1 to 12 carbon atoms, particularly preferably 1 to 8 carbon atoms, the examples of which include methyl, ethyl, iso-propyl, tert-butyl, n-octyl, n-decyl, n-hexadecyl, cyclopropyl, cyclopentyl and cyclohexyl), an alkylsilyl group (preferably, an alkylsilyl group having 1 to 20 carbon atoms, more preferably 1 to 10 carbon atoms, the examples of which include trimethylsilyl and triethylsilyl), an arylsilyl group (preferably, an arylsilyl group having 6 to 50 carbon atoms, more preferably 6 to 30 carbon atoms, the examples of which include a triphenylsilyl group and a trinaphthylsilyl group), a substituted or unsubstituted amino group (preferably, an amino group having 0 to 20 carbon atoms, more preferably 0 to 12 carbon atoms, and particularly preferably 0 to 6 carbon atoms, the examples of which include amino, methylamino, dimethylamino, diethylamino, diphenylamino and dibenzylamino), an alkoxy group (preferably an alkoxy group having 1 to 20 carbon atoms, more preferably 1 to 12 carbon atoms, and particularly preferably 1 to 8 carbon atoms, the examples of which include methoxy, ethoxy and butoxy), an aryloxy group (preferably, an aryloxy group having 6 to 20 carbon atoms, more preferably 6 to 16 carbon atoms, and particularly preferably 6 to 12 carbon atoms, the examples of which include phenyloxy and 2-naphthyloxy), an acyl group (preferably, an acyl group having 1 to 20 carbon atoms, more preferably 1 to 16 carbon atoms, and particularly preferably 1 to 12 carbon atoms, the examples of which include acetyl, benzoyl, formyl and pivaloyl), an alkoxycarbonyl group (preferably, an alkoxycarbonyl group having 2 to 20 carbon atoms, more preferably 2 to 16 carbon atoms, and particularly preferably 2 to 12 carbon atoms, the examples of which include methoxycarbonyl and ethoxycarbonyl), an aryloxycarbonyl group (preferably, an aryloxycarbonyl group having 7 to 20 carbon atoms, more preferably 7 to 16 carbon atoms, and particularly preferably 7 to 10 carbon atoms, the examples of which include phenyloxycarbonyl), an acyloxy group (preferably, an acyloxy group having 2 to 20 carbon atoms, more preferably an acyloxy group having 2 to 16 carbon atoms, particularly preferably an acyloxy group having 2 to 10 carbon atoms, the examples of which include acetoxy and benzoyloxy), an acylamino group (preferably, an acylamino group having 2 to 20 carbon atoms, more preferably 2 to 16 carbon atoms, and particularly preferably 2 to 10 carbon atoms, the examples of which include acetylamino and benzoylamino), an alkoxycarbonylamino group (preferably, an alkoxycarbonylamino having 2 to 20 carbon atoms, more preferably 2 to 16 carbon atoms, particularly preferably having 2 to 12 carbon atoms, the examples of which include methoxycarbonylamino), an aryloxycarbonylamino group (preferably, an aryloxycarbonylamino group having 7 to 20 carbon atoms, more preferably having 7 to 16 carbon atoms, particularly preferably 7 to 12 carbon atoms, the examples of which include a phenyloxycarbonylamino group), a substituted or unsubstituted sulfonylamino group (preferably, a sulfonylamino group having 1 to 20 carbon atoms, more preferably sulfonylamino group having 1 to 16 carbon atoms, particularly preferably having 1 to 12 carbon atoms, the examples of which include methanesulfonylamiono and benzenesulfonylamino), a substituted or unsubstituted sulfamoyl group (preferably a sulfamoyl group having 0 to 20 carbon atoms, more preferably 0 to 16 carbon atoms, particularly preferably 0 to 12 carbon atoms, the examples of which include sulfamoyl, methylsulfamoyl, dimethylsulfamoyl and phenylsulfamoyl), a substituted or unsubstituted carbamoyl group (preferably, a carbamoyl group having 1 to 20 carbon atoms, more preferably 1 to 16 carbon atoms, particularly preferably having 1 to 12 carbon atoms, the examples of which include carbamoyl, methylcarbamoyl, diethylcarbamoyl and phenylcarbamoyl), an alkylthio group (preferably, an alkylthio group having 1 to 20 carbon atoms, more preferably 1 to 16 carbon atoms, and particularly preferably 1 to 12 carbon atoms, the examples of which include methylthio and ethylthio), an arylthio group (preferably, an arylthio group having 6 to 20 carbon atoms, more preferably 6 to 16 carbon atoms, and particularly preferably 6 to 12 carbon atoms, the examples of which include phenylthio), a substituted or unsubstituted sulfonyl group (preferably, a sulfonyl group having 1 to 20 carbon atoms, more preferably 1 to 16 carbon atoms, and particularly preferably 1 to 12 carbon atoms, the examples of which include methyl and tosyl), a substituted or unsubstituted sulfinyl group (preferably, a sulfinyl group having 1 to 20 carbon atoms, more preferably 1 to 16 carbon atoms, particularly preferably 1 to 12 carbon atoms, the examples of which include methanesulfinyl and benzensulfinyl), a substituted or unsubstituted ureido group (preferably, a ureido group having 1 to 20 carbon atoms, more preferably 1 to 16 carbon atoms, particularly preferably 1 to 12 carbon atoms, the examples of which include ureido, methylureido, and phenylureido), a substituted or unsubstituted phosphoric amide group (preferably, a phosphoric amide group having 1 to 20 carbon atoms, more preferably 1 to 16 carbon atoms, and particularly preferably 1 to 12 carbon atoms, the examples of which include diethylphosphoric amide and phenylphosphoric amide), a hydroxyl group, a mercapto group, a halogen atom (for example, a fluorine atom, a chlorine atom, a bromine atom, an iodine atom), a cyano group, a sulfo group, a carboxyl group, a nitro group, a hydroxamic acid group, a sulfino group, a hydrazino group, an imino group, a substituted or unsubstituted silyl group (preferably, a silyl group having 3 to 40 carbon atoms, more preferably 3 to 30 carbon atoms, and particularly preferably 3 to 24 carbon atoms, the examples of which include trimethylsilyl and triphenylsilyl).

These substituents may further be substituted. If there are two or more substituents, these substituents may be the same or different. If possible, these substituents may be bonded together to form a ring.

Of these substituents, an aryl group, an alkyl group, an alkylsilyl group and an arylsilyl group are preferable.

In a preferred embodiment, in formula (1), $R_1$ to $R_{10}$ are a hydrogen atom.

In a preferred embodiment, at least one of $R_{21}$ to $R_{25}$ is a substituted or unsubstituted fused aromatic ring having 10 to 20 ring carbon atoms and the others are a hydrogen atom.

In a preferred embodiment, in the formula (1), at least one of $R_{21}$ to $R_{25}$ is a substituted or unsubstituted naphthyl group or a substituted or unsubstituted phenanthryl group, and the others are a hydrogen atom.

Specific examples of the chrysene derivative are given below.

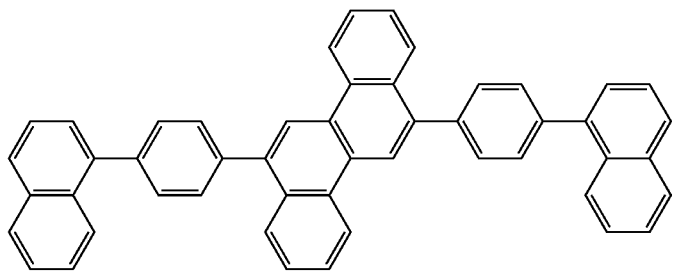

-continued
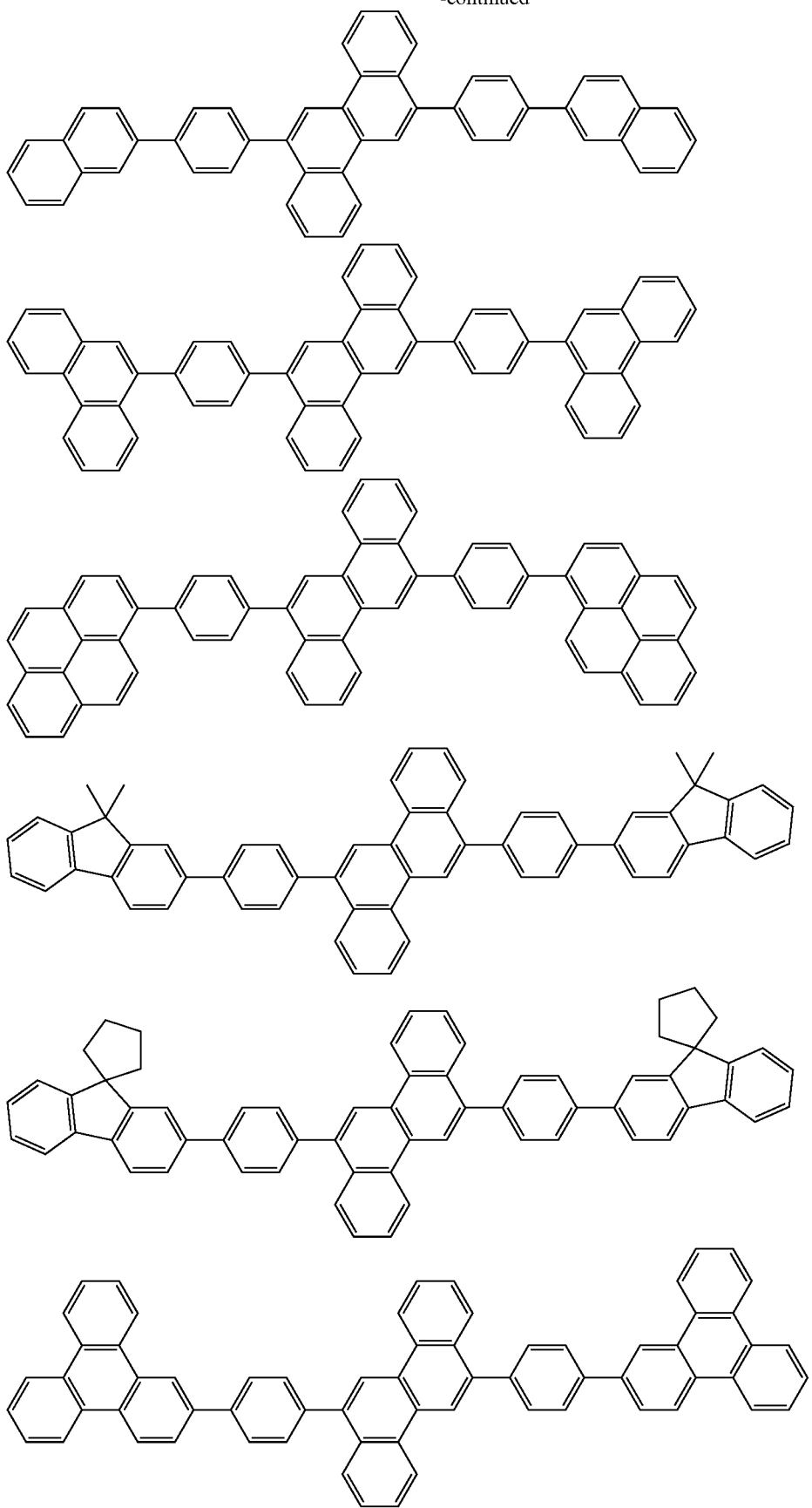

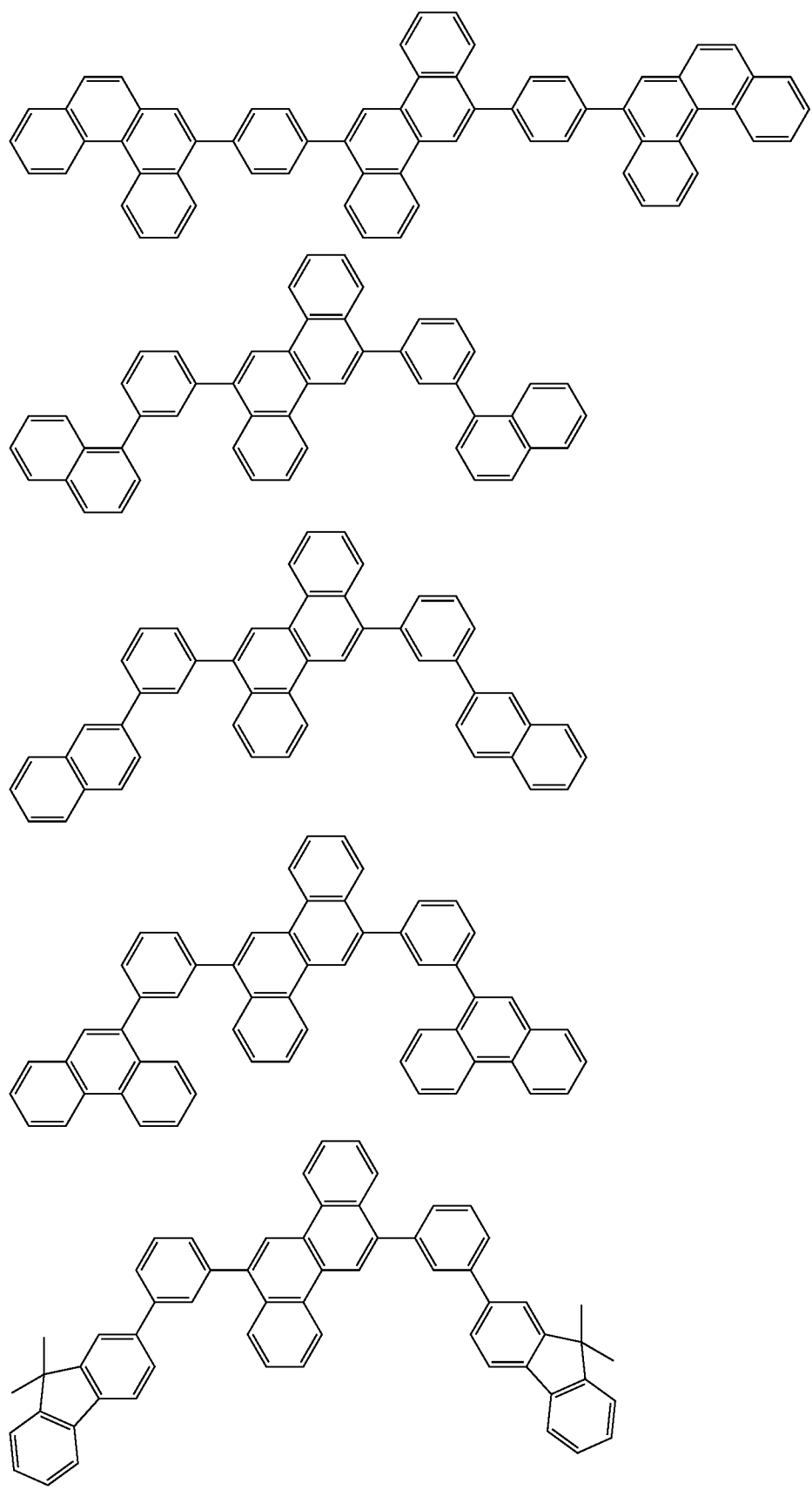

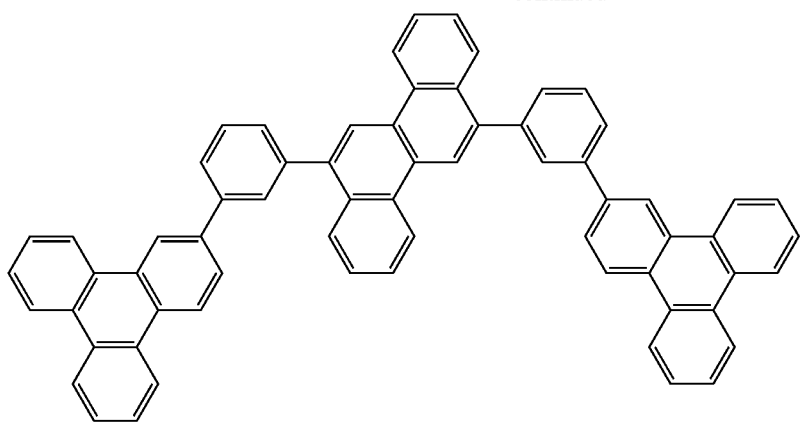
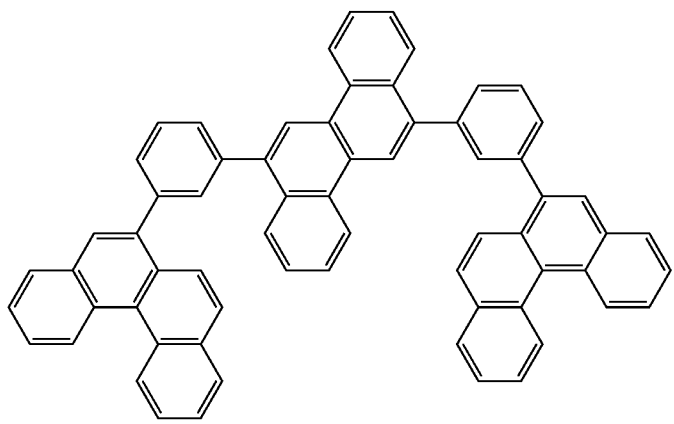
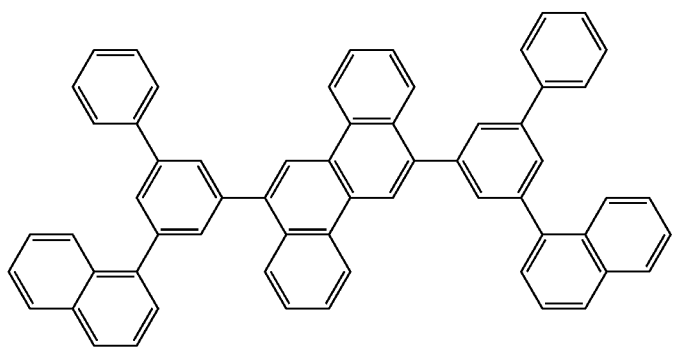
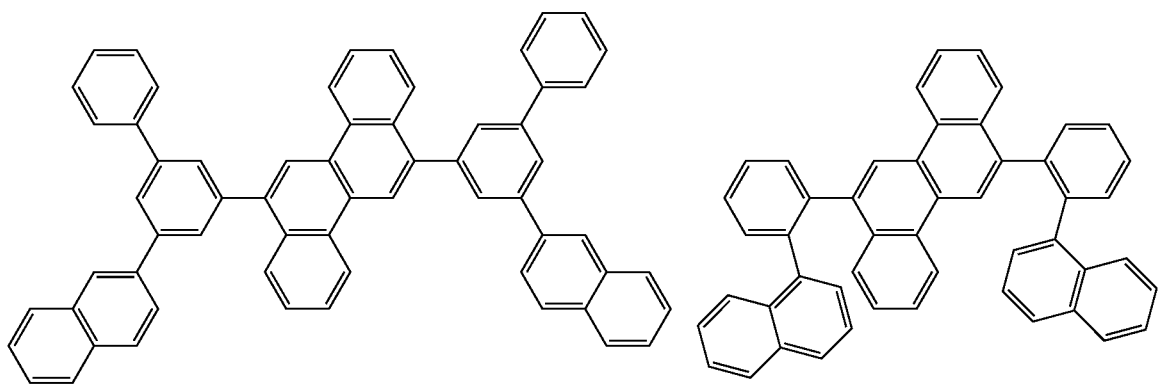

-continued
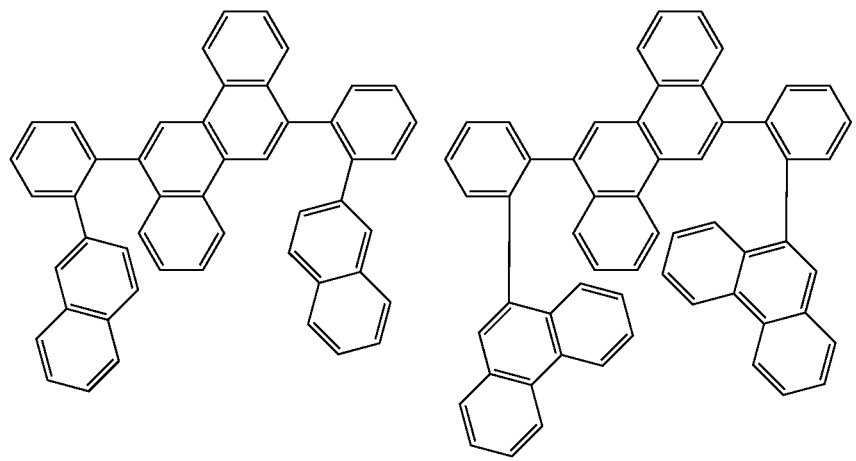
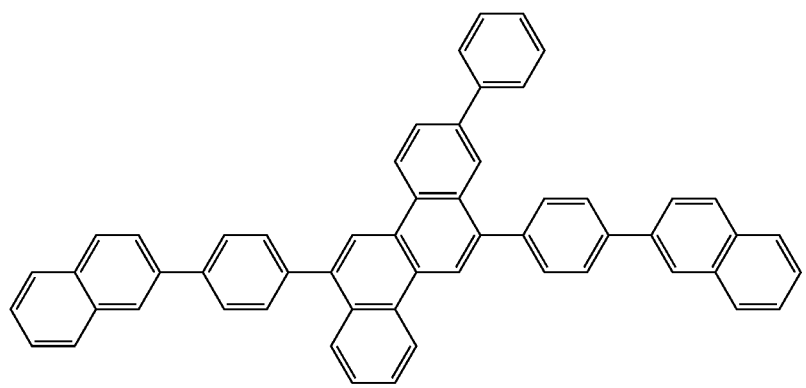
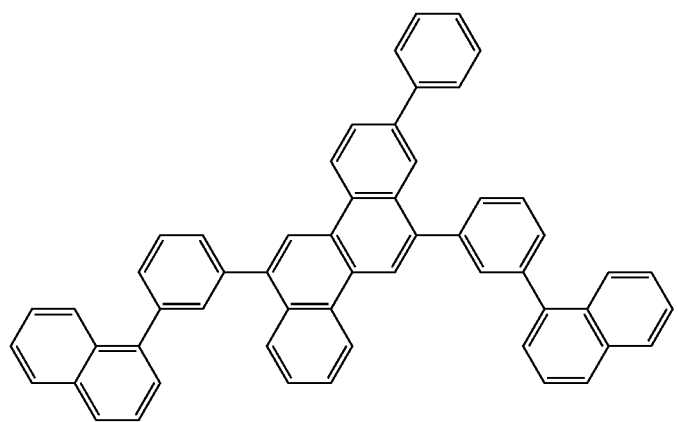

-continued
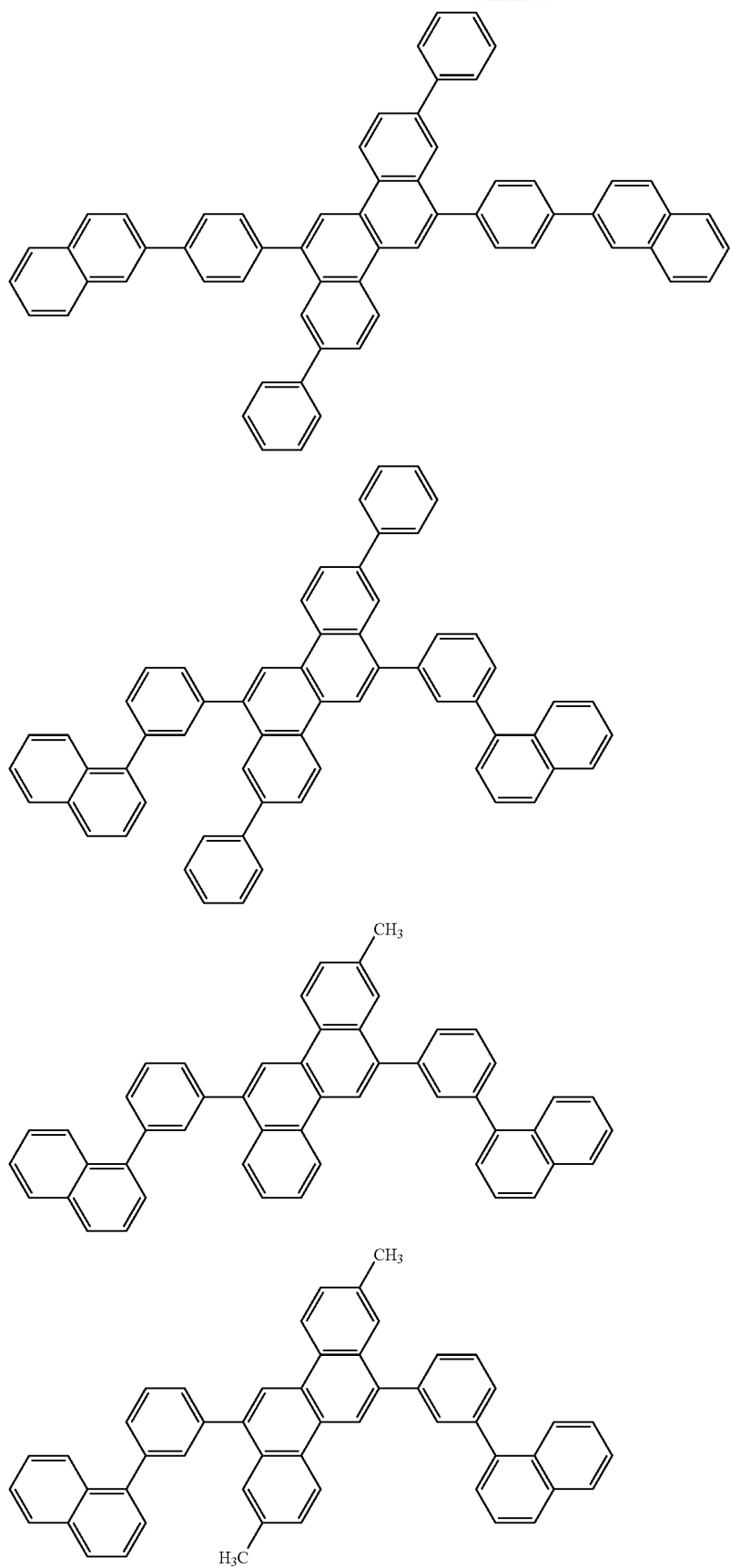

-continued
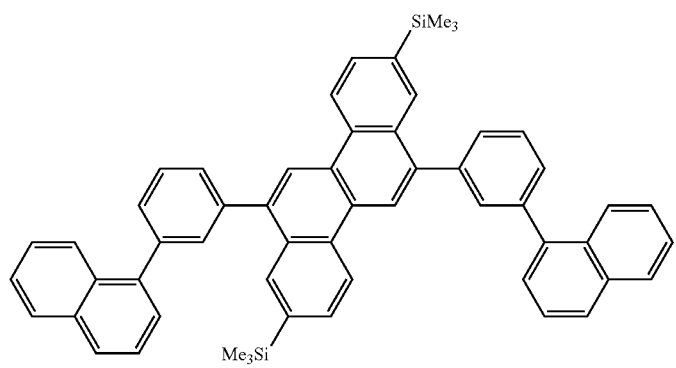
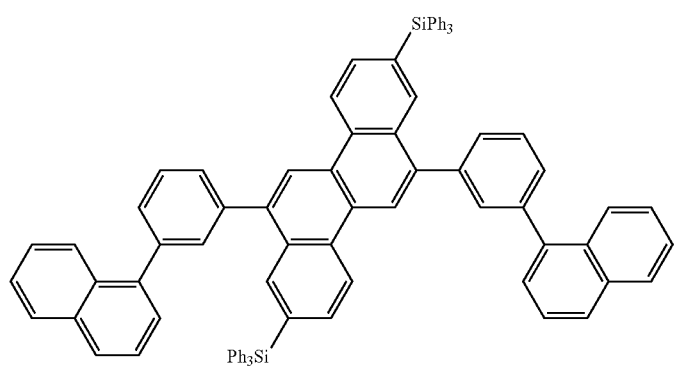
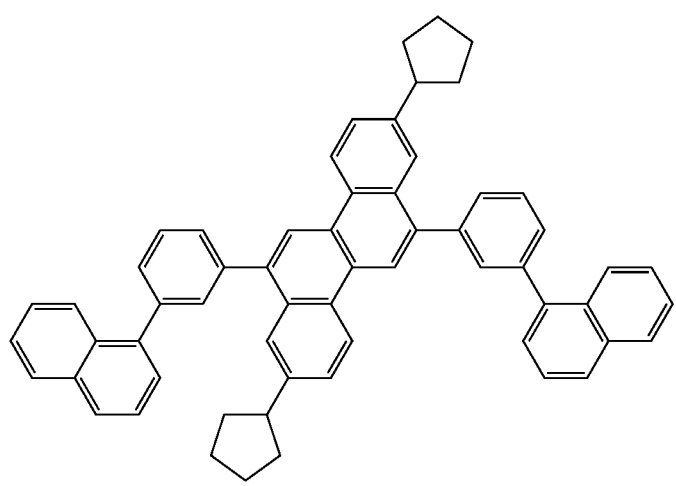
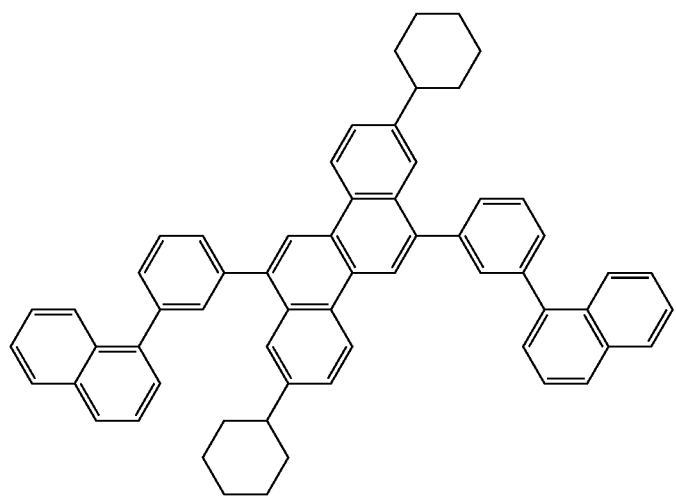

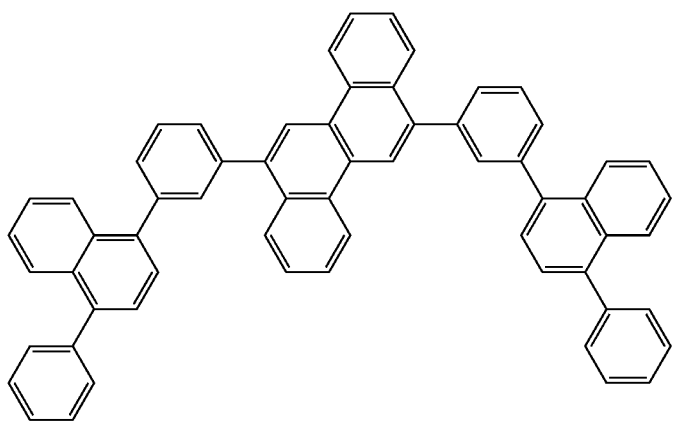
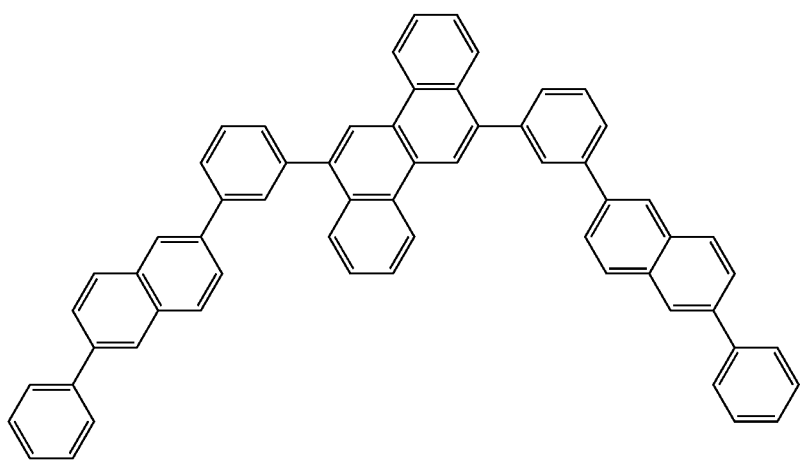
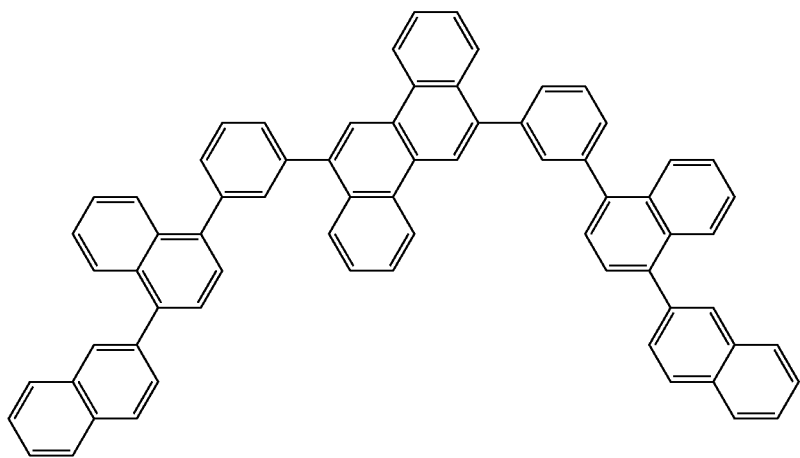

-continued
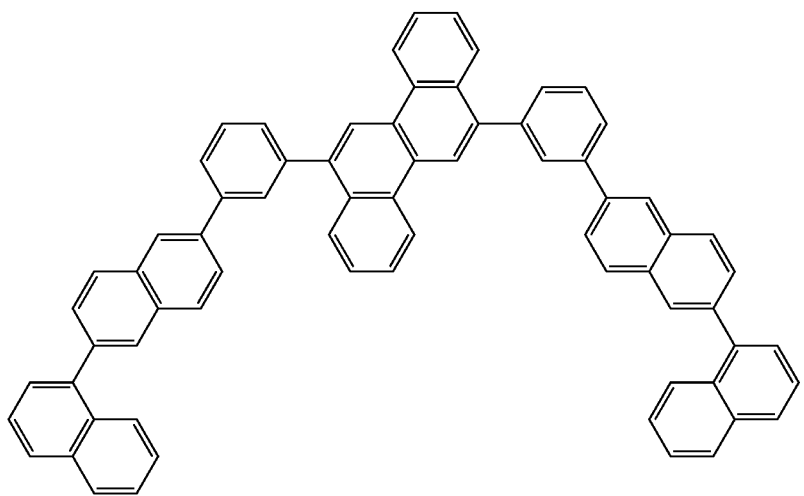
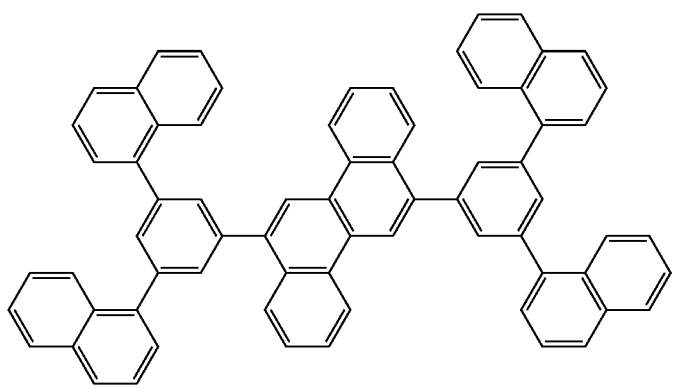
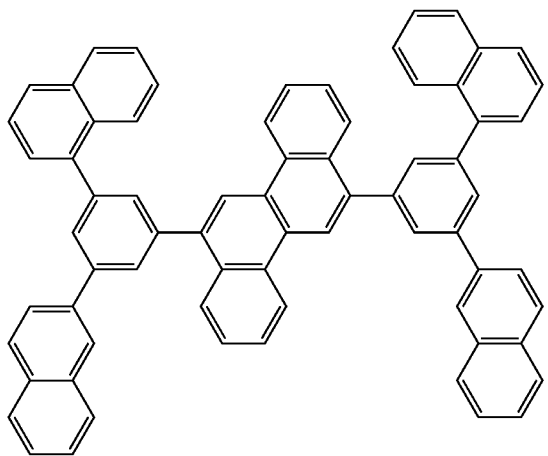

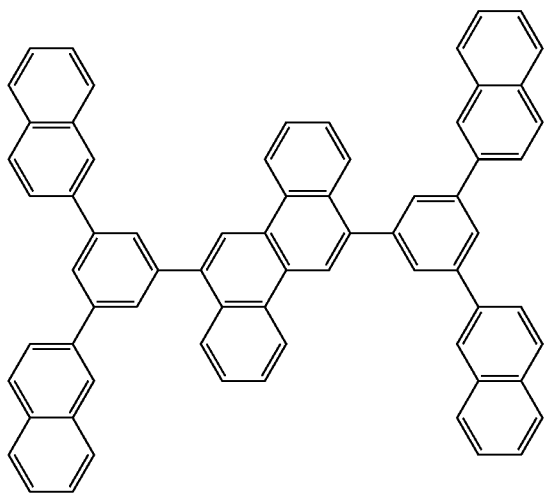
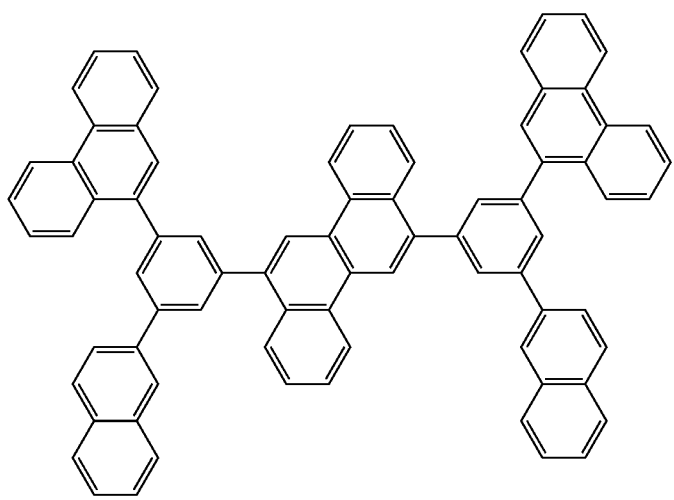
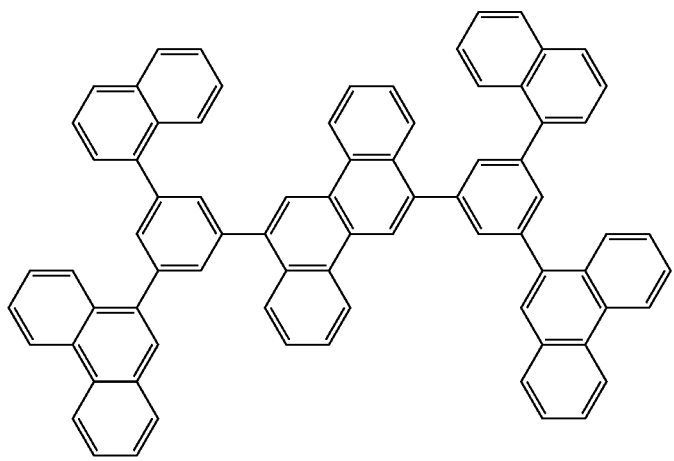

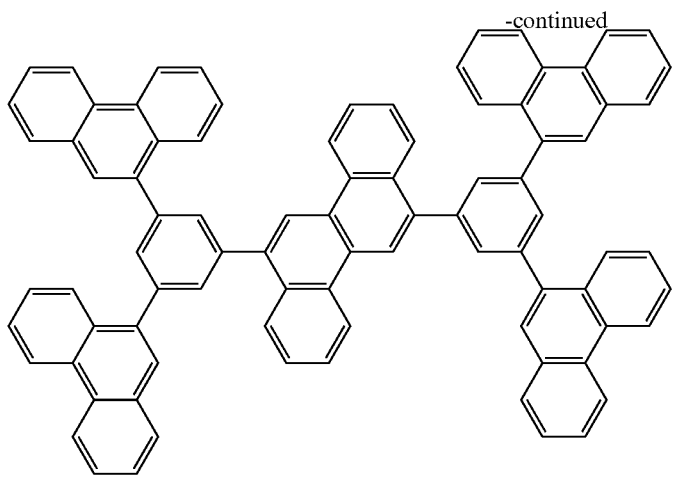

-continued wherein Me is a methyl group and Ph is a phenyl group.

The chrysene derivative of the invention can be preferably used as a material for an organic EL device, in particular, as an emitting material.

The organic EL device of the invention has an anode and a cathode, and one or more organic thin film layers including an emitting layer, disposed between the anode and the cathode. At least one of the organic thin film layers contains the chrysene derivative of the invention.

The representative configurations of the organic EL device of the invention are as follows.
(1) Anode/Emitting layer/Cathode
(2) Anode/Hole-injecting layer/Emitting layer/Cathode
(3) Anode/Emitting layer/Electron-injecting layer/Cathode
(4) Anode/Hole-injecting layer/Emitting layer/Electron-injecting layer/Cathode
(5) Anode/Organic semiconductor layer/Emitting layer/Cathode
(6) Anode/Organic semiconductor layer/Electron-barrier layer/Emitting layer/Cathode
(7) Anode/Organic semiconductor layer/Emitting layer/Adhesion-improvement layer/Cathode
(8) Anode/Hole-injecting layer/Hole-transporting layer/Emitting layer/Electron-injecting layer/Cathode
(9) Anode/Insulating layer/Emitting layer/Insulating layer/Cathode
(10) Anode/Inorganic semiconductor layer/Insulating layer/Emitting layer/Insulating layer/Cathode
(11) Anode/Organic semiconductor layer/Insulating layer/Emitting layer/Insulating layer/Cathode
(12) Anode/Insulating layer/Hole-injecting layer/Hole-transporting layer/Emitting layer/Insulating layer/Cathode
(13) Anode/Insulating layer/Hole-injecting layer/Hole-transporting layer/Emitting layer/Electron-injecting layer/Cathode The configuration of the organic EL device is not limited to the above. Of these, normally, the configuration indicated by (8) can be preferably used.

FIG. 1 shows the configuration shown in (8). This organic EL device has an anode 10 and a cathode 20, a hole-injecting layer 30, a hole-transporting layer 32, an emitting layer 34 and an electron-injecting layer 36 interposed between the anode 10 and the cathode 20. The hole-injecting layer 30, the hole-transporting layer 32, the emitting layer 34 and the electron-injecting layer 36 correspond to a plurality of organic thin film layers. At least one of the organic thin film layers 30, 32, 34 and 36 contains the chrysene derivative of the invention.

In the organic EL device of the invention, the chrysene derivative of the invention may be used in any of the above-mentioned organic thin film layers. However, it is preferred that the chrysene derivative be used in the emitting layer. In each of the organic thin film layers, the chrysene derivative of the invention may be used alone or in combination with other compounds. In the device of the invention, it is preferred that the emitting layer contain the chrysene derivative of the invention as a host material and contain at least one of a fluorescent dopant and a phosphorescent dopant.

In the invention, it is preferred that the emitting layer consist essentially of the chrysene derivative and the above-mentioned dopant.

The content of the chrysene derivative of the invention in the organic thin film layer is preferably 30 to 100 mol %.

Then, an explanation will be made on each element of the organic EL device.

The organic EL device is normally formed on a substrate. The substrate supports the organic EL device. It is preferable to use a smooth substrate. When light is outcoupled through this substrate, it is preferred that the substrate be light transmissible and have a transmittance of 50% or more for light in a visible range with a wavelength of 400 to 700 nm.

Preferred examples of such transparent substrate include a glass plate, a synthetic resin plate or the like. Examples of the glass plate include plates of soda-lime glass, barium/strontium-containing glass, lead glass, aluminosilicate glass, borosilicate glass, barium borosilicate glass and quartz. As the synthetic resin plates, plates of a polycarbonate resin, an acryl resin, a polyethyleneterephthalate resin, a polyether sulfide resin and a polysulfonic resin can be given.

It is effective that the anode inject holes to the hole-injecting layer, the hole-transporting layer and the emitting layer, and have a work function of 4.5 eV or more. Specific examples of the anode material include indium oxide tin (ITO), a mixture of indium oxide and zinc oxide (IZO), a mixture of ITO and cerium oxide (ITCO), a mixture of IZO and cerium oxide (IZCO), a mixture of indium oxide and cerium oxide (ICO), a mixture of zinc oxide and aluminum oxide (AZO), tin oxide (NESA), gold, silver, platinum and copper.

The anode can be produced from these electrode materials by a vapor deposition method, a sputtering method or the like.

In the case where emission from the emitting layer is outcoupled through the anode, the transmittance of the anode to the emission is preferably more than 10%. The sheet resistance of the anode is preferably several hundred Ω/□ or less. The film thickness of the anode, which varies depending upon the material thereof, is usually from 10 nm to 1 μm, preferably from 10 to 200 nm.

The emitting layer has the following functions.
(i) Injection function: function of allowing injection of holes from the anode or hole-injecting layer and injection of electrons from the cathode or electron-injecting layer upon application of an electric field
(ii) Transporting function: function of moving injected carriers (electrons and holes) due to the force of an electric field
(iii) Emitting function: function of combining electrons and holes to cause emission As the method of forming the emitting layer, a known method such as vapor deposition, spin coating, or an LB method may be applied. It is preferable that the emitting layer be a molecular deposition film. The molecular deposition film means a film formed by depositing material compounds in a vapor phase condition or a film formed by solidifying material compounds in a solution or liquid phase condition. The molecular deposition film is distinguished from a thin film (molecular accumulation film) formed using the LB method by the difference in aggregation structure or higher order structure or the difference in function due to the difference in structure.

The emitting layer may also be formed by dissolving a binder such as a resin and a material compound in a solvent to obtain a solution, and forming a thin film from the solution by a spin coating method or the like.

As the emitting material used for the emitting layer, anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenylbutadiene, coumarin, oxadiazole, aldazine, bisbenzoxazoline, bisstyryl, pyrazine, cyclopentadiene, a quinoline metal complex, an aminoquinoline metal complex, a benzoquinoline metal complex, imine, diphenyl ethylene, vinylanthracene, diaminocarbazole, pyran, thiopyran, polymethine, merocyanine, an imidazole chelate oxanoid compound, quinacridone, rubrene, derivatives thereof, a fluorescent pigment and like can be given. Note that the emitting material are not limited to these compounds.

As the host material for use in the emitting layer, the compounds represented by the following formulas (i) to (ix) are preferred.

Asymmetrical anthracene represented by the following formula (i):

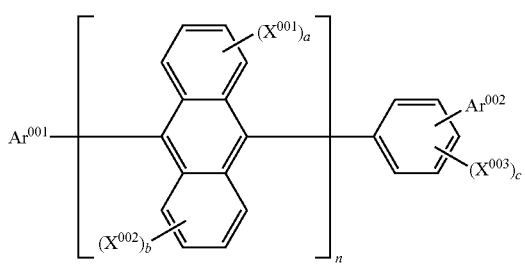

wherein $Ar^{001}$ is a substituted or unsubstituted fused aromatic group having 10 to 50 ring carbon atoms, $Ar^{002}$ is a substituted or unsubstituted aromatic group having 6 to 50 ring carbon atoms, $X^{001}$ to $X^{003}$ are independently a substituted or unsubstituted aromatic group having 6 to 50 ring carbon atoms, a substituted or unsubstituted aromatic heterocyclic group having 5 to 50 atoms that form a ring (hereinafter referred to as ring atoms), a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a carboxyl group, a halogen atom, a cyano group, a nitro group or a hydroxyl group. a, b and c are each an integer of 0 to 4. n is an integer of 1 to 3. When n is two or more, the groups in [ ] may be the same or different.

Asymmetrical monoanthracene derivatives represented by the following formula (ii):

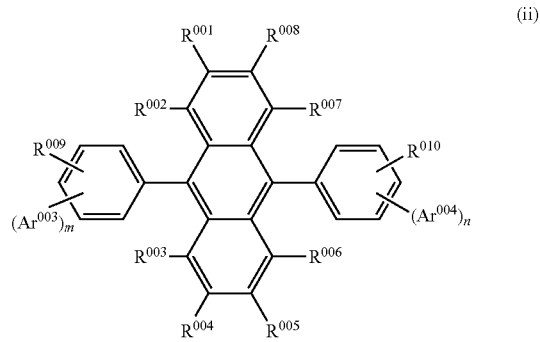

wherein $Ar^{003}$ and $Ar^{004}$ are independently a substituted or unsubstituted aromatic ring group having 6 to 50 ring carbon atoms, and m and n are each an integer of 1 to 4, provided that in the case where m=n=1 and $Ar^{003}$ and $Ar^{004}$ are symmetrically bonded to the benzene rings, $Ar^{003}$ and $Ar^{004}$ are not the same, and in the case where m or n is an integer of 2 to 4, m is different from n; and $R^{001}$ to $R^{010}$ are independently a hydrogen atom, a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group and a hydroxyl group.

Asymmetrical pyrene derivatives represented by the following formula (iii):

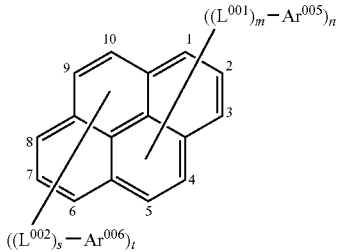

(iii)

wherein $Ar^{005}$ and $Ar^{006}$ are independently a substituted or unsubstituted aromatic group having 6 to 50 ring carbon atoms; $L^{001}$ and $L^{002}$ are each a substituted or unsubstituted phenylene group, a substituted or unsubstituted naphthalenylene group, a substituted or unsubstituted fluorenylene group, or a substituted or unsubstituted dibenzosilolylene group;

m is an integer of 0 to 2, n is an integer of 1 to 4, s is an integer of 0 to 2, and t is an integer of 0 to 4;

$L^{001}$ or $Ar^{005}$ bonds at any one position of 1 to 5 of the pyrene, and $L^{002}$ or $Ar^{006}$ bonds at any one position of 6 to 10 of the pyrene; provided that when n+t is an even number, $Ar^{005}$, $Ar^{006}$, $L^{001}$ and $L^{002}$ satisfy the following (1) or (2):
(1) $Ar^{005} \neq Ar^{006}$ and/or $L^{001} \neq L^{002}$ where ≠ means these substituents are groups having different structures from each other.
(2) when $Ar^{005}=Ar^{006}$ and $L^{001} \neq L^{002}$,
  (2-1) m≠s and/or n≠t, or
  (2-2) when m=s and n=t,
    (2-2-1) when $L^{001}$ and $L^{002}$ or pyrene are independently bonded to different bonding positions of $Ar^{005}$ and $Ar^{006}$, or (2-2-2) when $L^{001}$ and $L^{002}$ or pyrene are bonded to the same position of $Ar^{005}$ and $Ar^{006}$, or (2-2-2) when $L^{001}$ and $L^{002}$ or pyrene are bonded to the same position of $Ar^{005}$ and $Ar^{006}$, the positions of the substitution of $L^{001}$ and $L^{002}$ or $Ar^{005}$ and $Ar^{006}$ at pyrene are neither the $1^{st}$ position and the $6^{th}$ position, nor the $2^{nd}$ position and the $7^{th}$ position.

Asymmetrical anthracene derivatives represented by the following formula (iv):

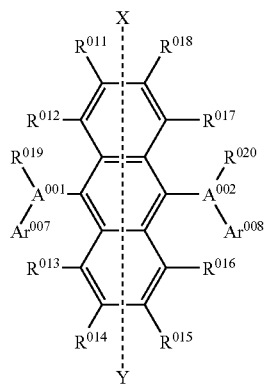

(iv)

wherein $A^{001}$ and $A^{002}$ are independently a substituted or unsubstituted fused aromatic ring group having 10 to 20 ring carbon atoms, $Ar^{007}$ and $Ar^{008}$ are independently a hydrogen atom or a substituted or unsubstituted aromatic ring group with 6 to 50 ring carbon atoms, $R^{011}$ to $R^{020}$ are independently a hydrogen atom or a substituted or unsubstituted aromatic ring group having 6 to 50 ring carbon atoms, a substituted or unsubstituted aromatic heterocyclic group having 5 to 50 ring atoms, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 ring atoms, a substituted or unsubstituted arylthio group having 5 to 50 ring atoms, a substituted or unsubstituted alkoxycarbonyl group having 1 to 50 carbon atoms, a substituted or unsubstituted silyl group, a carboxyl group, a halogen atom, a cyano group, a nitro group or a hydroxyl group, and each of $Ar^{007}$, $Ar^{008}$, $R^{019}$ and $R^{020}$ may be plural, and adjacent groups thereof may form a saturated or unsaturated ring structure, provided that groups do not symmetrically bond to 9 and 10 positions of the central anthracene with respect to X-Y axis in the formula (iv).

Anthracene derivatives represented by the following formula (v):

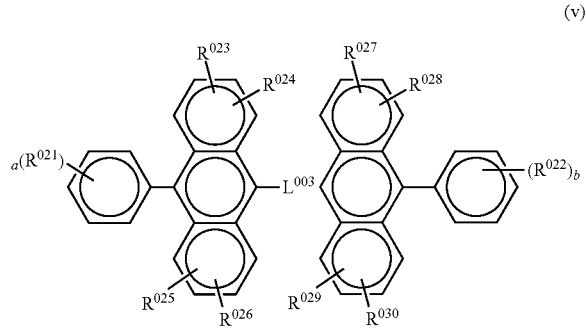

(v)

wherein $R^{021}$ to $R^{030}$ are independently a hydrogen atom, an alkyl group, a cycloalkyl group, an aryl group which may be substituted, an alkoxy group, an aryloxy group, an alkylamino group, an alkenyl group, an arylamino group or a heterocyclic group which may be substituted; a and b are each an integer of 1 to 5; when they are 2 or more, $R^{021}$s or $R^{022}$s may be the same or different, or $R^{021}$s or $R^{022}$s may be bonded together to form a ring; $R^{023}$ and $R^{024}$, $R^{025}$ and $R^{026}$, $R^{027}$ and $R^{028}$, or $R^{029}$ and $R^{030}$ may be bonded together to form a ring; and $L^{003}$ is a single bond, —O—, —S—, —N(R)— (R is an alkyl group or a substituted or unsubstituted aryl group), an alkylene group or an arylene group.

Anthracene derivatives represented by the following formula (vi):

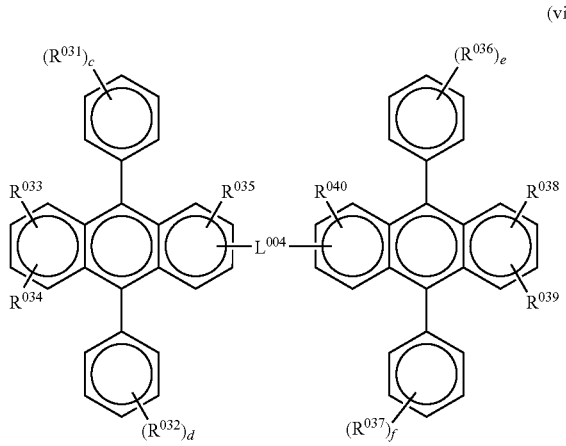

(vi)

wherein $R^{031}$ to $R^{040}$ are independently a hydrogen atom, an alkyl group, a cycloalkyl group, an aryl group, an alkoxy group, an aryloxy group, an alkylamino group, an arylamino group or a heterocyclic group which may be substituted; c, d, e and f are each an integer of 1 to 5; when they are 2 or more, $R^{031}$s, $R^{032}$s, $R^{036}$s or $R^{037}$s may be the same or different, $R^{031}$s, $R^{032}$s, $R^{033}$s or $R^{037}$s may be bonded to each other to form a ring, or $R^{033}$ and $R^{034}$, or $R^{039}$ and $R^{040}$ may be bonded to each other to form a ring; and $L^{004}$ is a single bond, —O—, —S—, —N(R)— (R is an alkyl group or a substituted or unsubstituted aryl group), an alkylene group or an arylene group.

Spirofluorene derivatives represented by the following formula (vii):

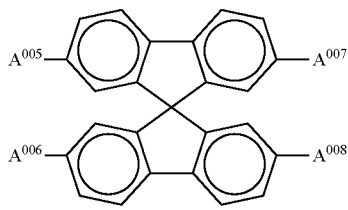

(vii)

wherein $A^{005}$ to $A^{008}$ are independently a substituted or unsubstituted biphenyl group or a substituted or unsubstituted naphthyl group.

Fused ring-containing compounds represented by the following formula (viii):

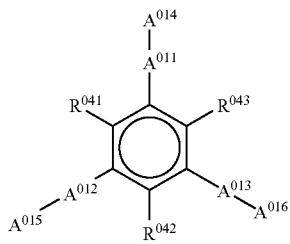

(viii)

wherein $A^{011}$ to $A^{013}$ is the same divalent group as $L_1$ in the formula (1), and $A^{014}$ to $A^{016}$ are the same substituents as Ra in the formula (1), $R^{041}$ to $R^{043}$ are independently a hydrogen atom, alkyl group having 1 to 6 carbon atoms, cycloalkyl group having 3 to 6 carbon atoms, alkoxy group having 1 to 6 carbon atoms, aryloxy group having 5 to 18 carbon atoms, aralkyloxy group having 7 to 18 carbon atoms, arylamino group having 5 to 16 carbon atoms, nitro group, cyano group, ester group having 1 to 6 carbon atoms, or a halogen atom, provided that at least one of $A^{011}$ to $A^{016}$ is a group having a fused aromatic ring with three or more rings.

Fluorene compounds represented by the following formula (ix):

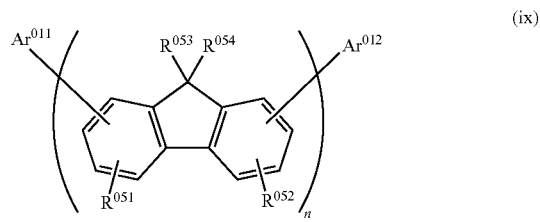

(ix)

wherein $R^{051}$ and $R^{052}$ are a hydrogen atom, a substituted or unsubstituted alkyl group, a substituted or unsubstituted aralkyl group, a substituted or unsubstituted aryl group, a substituted or unsubstituted heterocyclic group, substituted amino group, cyano group, or a halogen atom; $R^{051}$s or $R^{052}$s bonded to different fluorene groups may be the same or different, and $R^{051}$ and $R^{052}$ bonded to a single fluorene group may be the same or different; $R^{053}$ and $R^{054}$ are a hydrogen atom, a substituted or unsubstituted alkyl group, substituted or unsubstituted aralkyl group, substituted or unsubstituted aryl group, or substituted or unsubstituted heterocyclic group, provided that $R^{053}$s or $R^{054}$s bonded to different fluorene groups may be the same or different, and $R^{053}$ and $R^{054}$ bonded to a single fluorene group may be the same or different; $Ar^{011}$ and $Ar^{012}$ are a substituted or unsubstituted fused polycyclic aromatic group with a total number of benzene rings of three or more or a substituted or unsubstituted fused polycyclic heterocyclic group which is bonded to the fluorene group at carbon and has a total number of benzene rings and heterocyclic rings of three or more, provided that $Ar^{001}$ and $Ar^{012}$ may be the same or different; and n is an integer of 1 to 10.

Specific examples of the host compounds when a phosphorescent dopant is used include carbazole, triazole, oxazole, oxadiazole, imidazole, polyarylalkane, pyrazoline, pyrazolone, phenylanediamine, arylamine, amino-substituted calcone, styryl anthracene, fluorenone, hydrazone, stilbene and silazane derivatives; aromatic tertiary amine, styrylamine, aromatic dimethylidene and porphyrin compounds; anthraquinodimethane, anthrone, diphenylquinone, thiopyrandioxide, carbodiimide, fluoreniridenemethane and distyrylpyrazine derivatives; heterocyclic tetracarboxylic anhydrides such as naphthaleneperylene; phthalocyanine derivatives; metal complexes of 8-quinolinol derivatives; various metal complex polysilane compounds represented by metal complexes having metal phthalocyanine, benzoxazole or benzothiaole as a ligand; electroconductive macromolecular oligomers such as poly(N-vinylcarbazole) derivatives, aniline copolymers, thiophene oligomers and polythiophene; and macromolecular compounds such as polythiophene, polyphenylene, polyphenylenevinylene and polyfluorene derivatives. Host compounds can be used individually or as a combination of two or more kinds.

Specific compounds shown below can be exemplified.

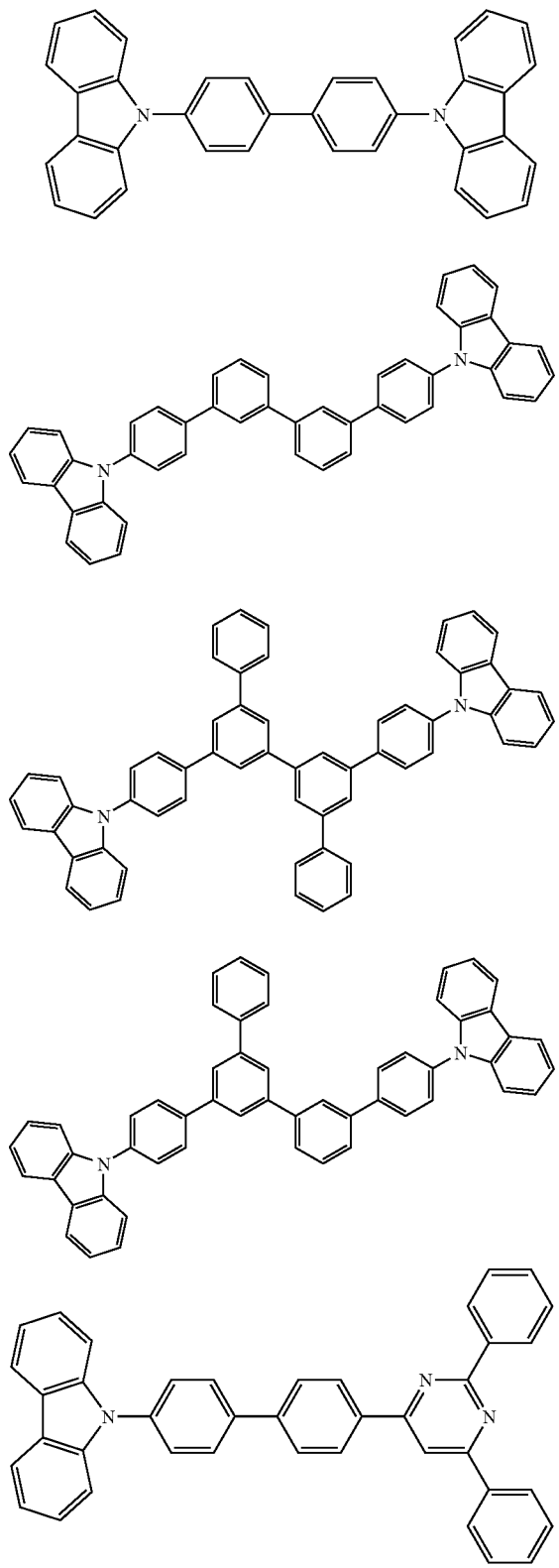

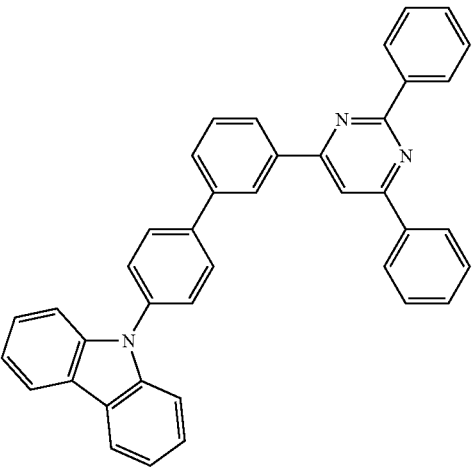

In the organic EL device of the invention, it is preferred that the emitting layer contain, as the host, the emitting material of the invention, and at least one of a phosphorescent dopant and a fluorescent dopant. An emitting layer containing these dopants may be stacked on the emitting layer containing the compound of the invention.

A phosphorescent dopant is a compound that can emit light from triplet excitons. Although there are no specific restrictions on the dopant as long as light is emitted from excitons, it is preferred that a phosphorescent dopant is a metal complex which contains at least one metal selected from Ir, Pt, Os, Au, Cu, Re and Ru. A porphyrin metal complex or an ortho-metalated complex is preferable. The phosphorescent compound may be used alone or in combination of two or more.

Since the chrysene derivative of the invention has a triplet energy level of 2.5 eV or less, it is preferable to use a phosphorescent dopant which can emit light with energy of 2.5 eV or less. Specifically, a phosphorescent dopant having an emission spectrum having a maximum peak at 520 to 700 nm is preferable.

As a porphyrin metal complex, a porphyrin platinum complex is preferable.

There are various ligands forming an ortho-metalated metal complex. Preferable ligands include a compound which has a phenylpyridine skeleton, a bipyridil skeleton or a phenanthroline skeleton, 2-phenylpyridine, 7,8-benzoquinoline, 2-(2-thienyl)pyridine, 2-(1-naphtyl)pyridine and 2-phenylquinoline derivatives. These ligands may have substituents, if necessary. Fluorides and derivatives with a trifluoromethyl group introduced are particularly preferable as a blue dopant. As an auxiliary ligand, preferred are ligands other than the above-mentioned ligands, such as acetylacetonate and picric acid, may be contained.

Specific examples of the metal complex include the following compounds. In the invention, it is preferable to combine the metal complex with a phosphorescent dopant which emits light in the red region. The metal complex is not limited to those given below, and an appropriate metal complex can be selected according to the required emission color, the device performance and the host compound used.

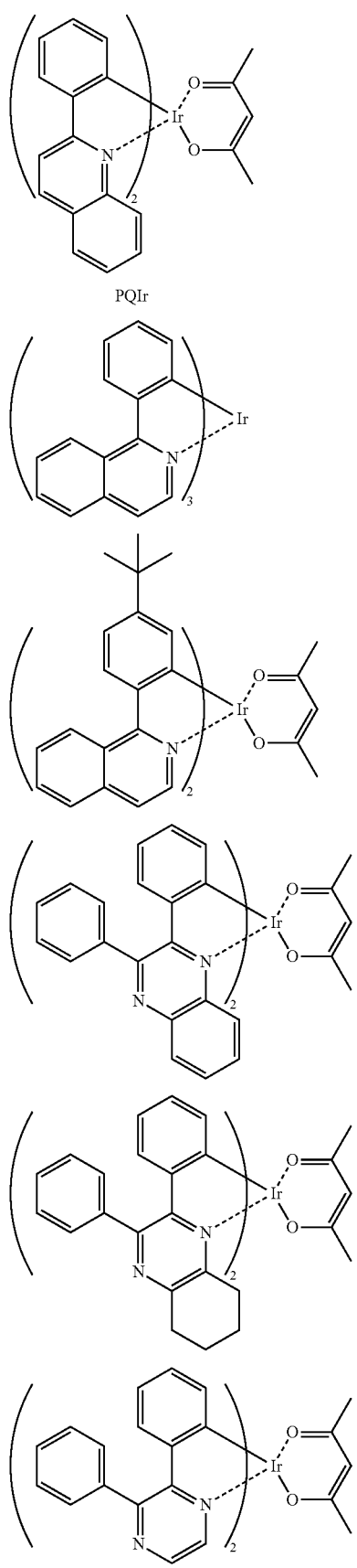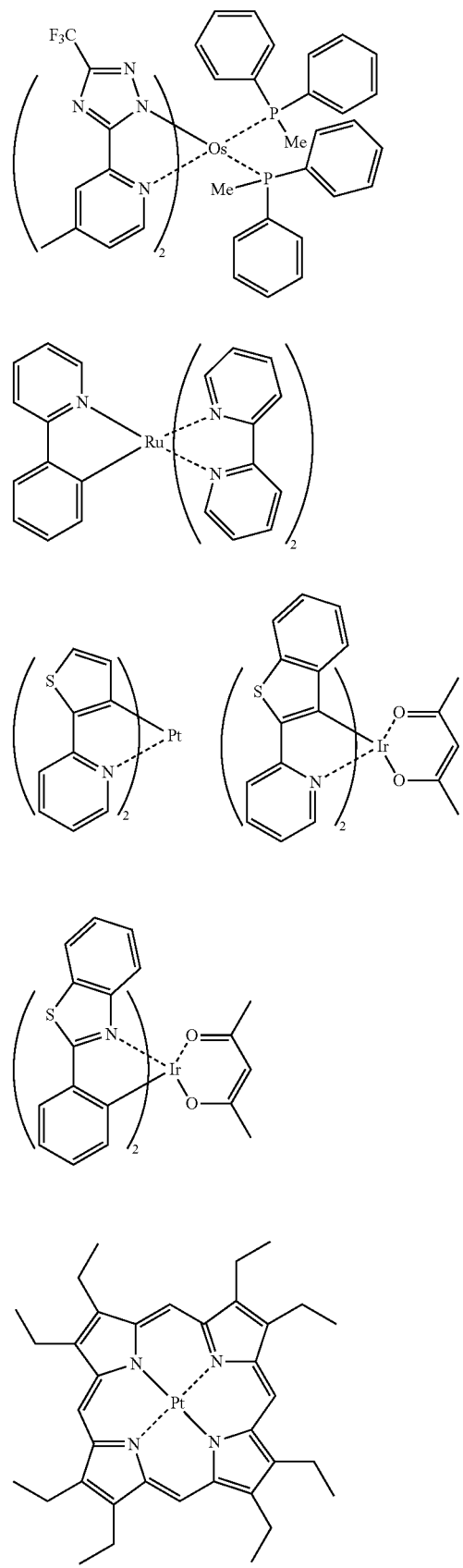

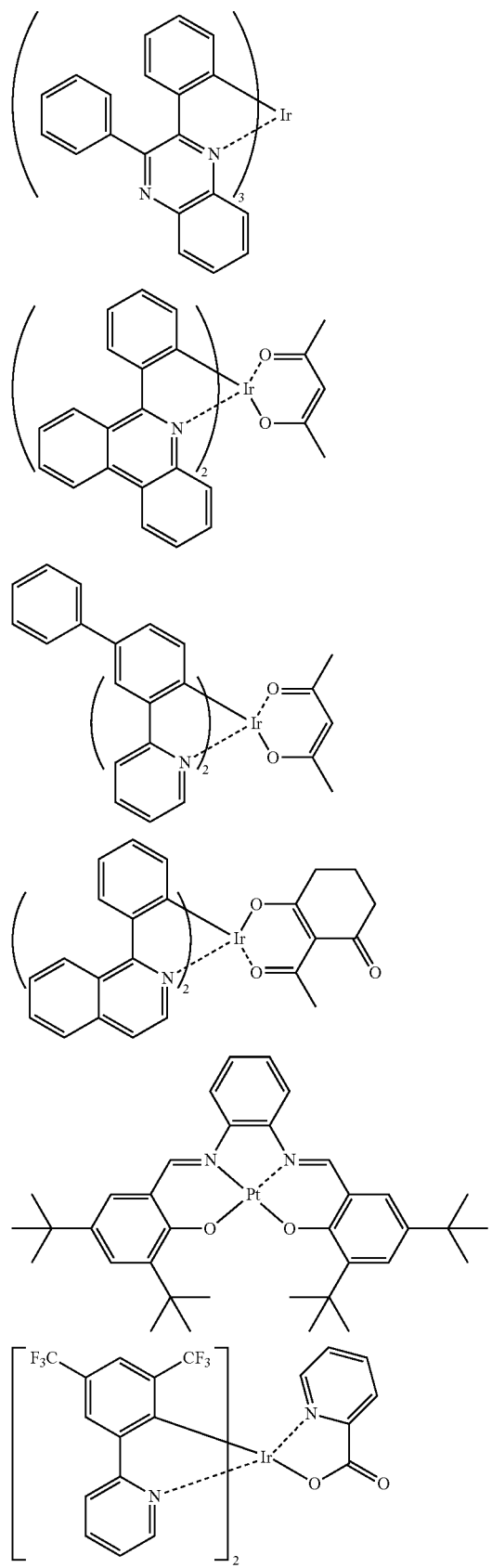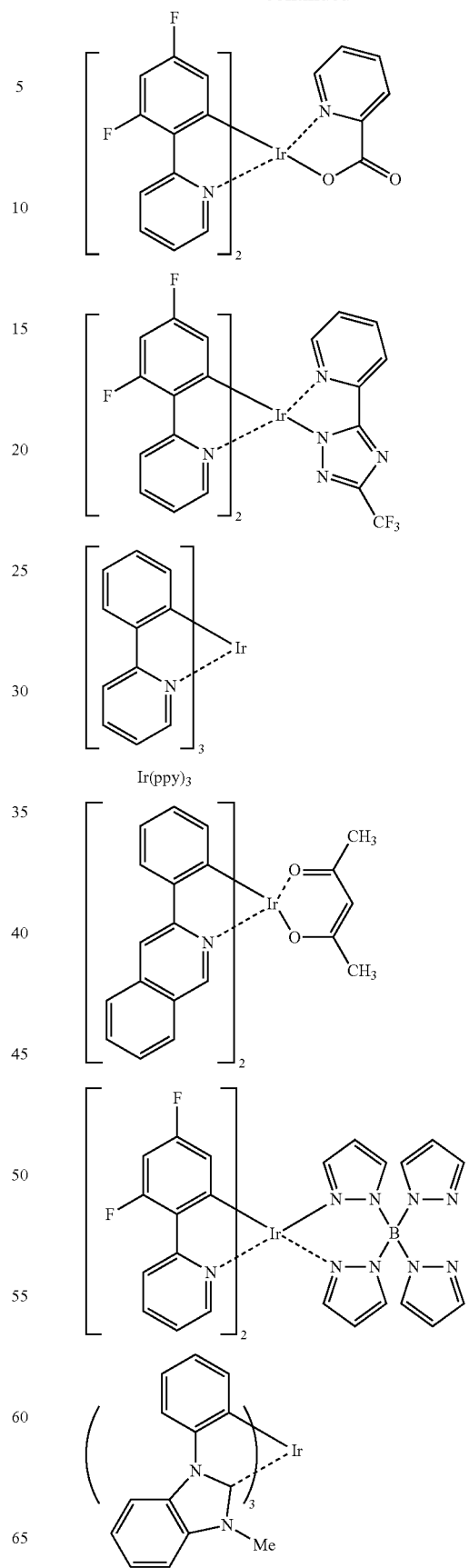
Ir(ppy)₃

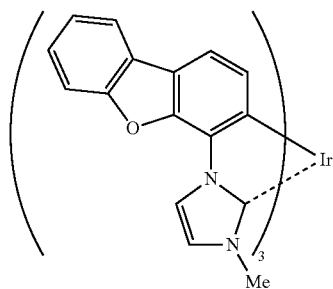
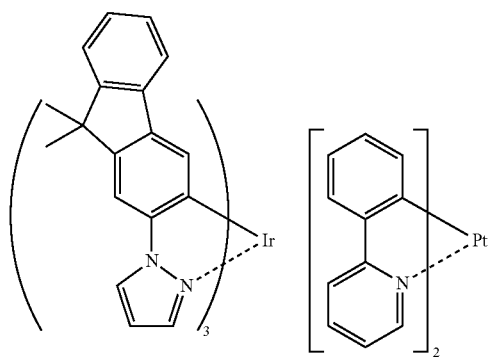
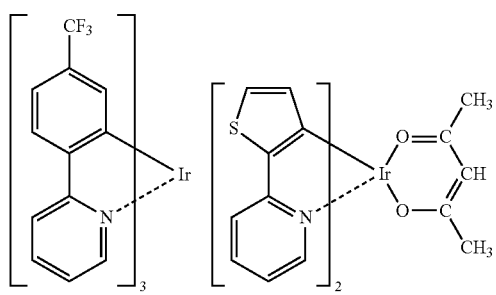
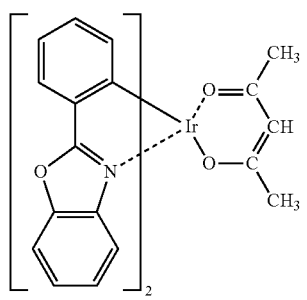
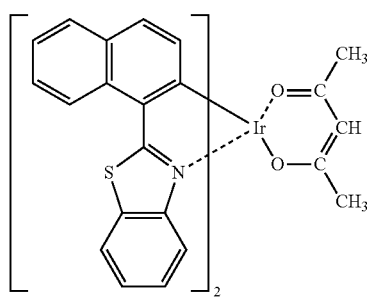
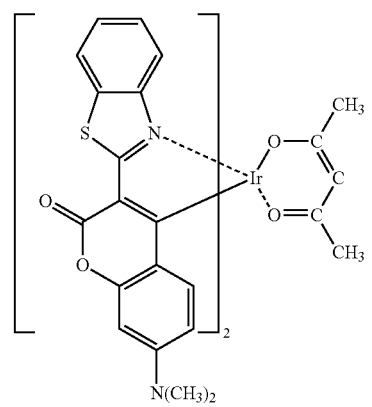
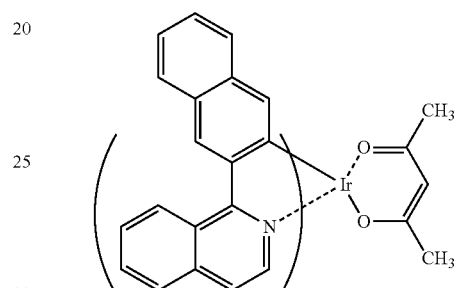
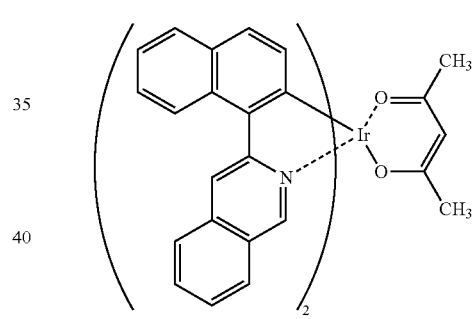
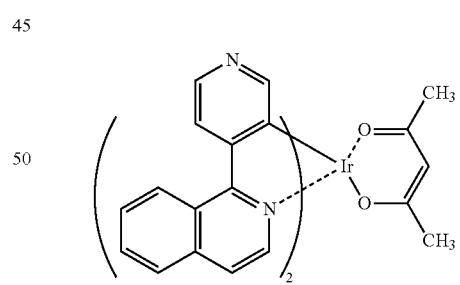
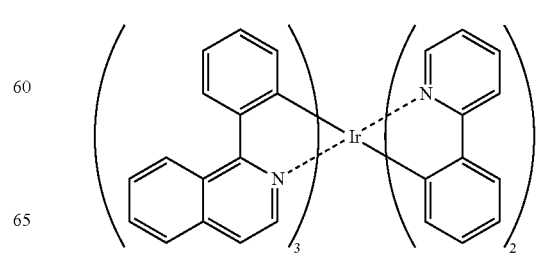

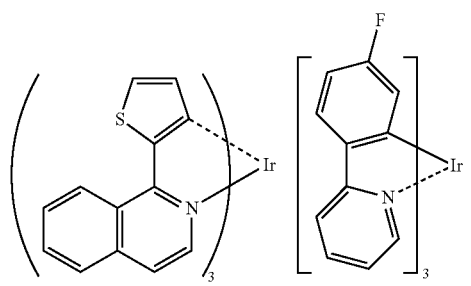
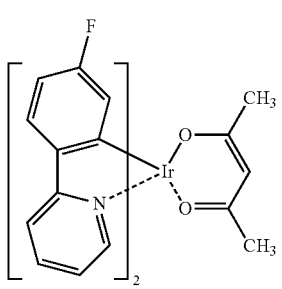
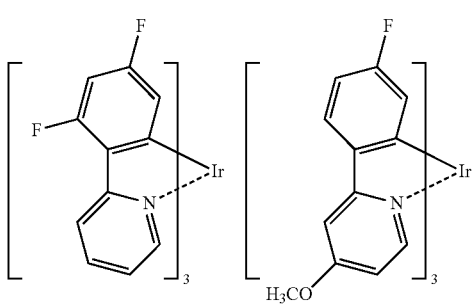
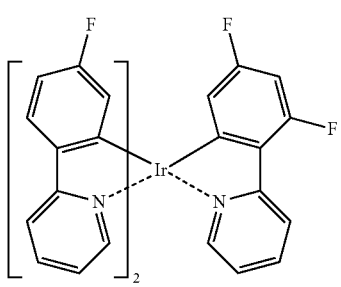
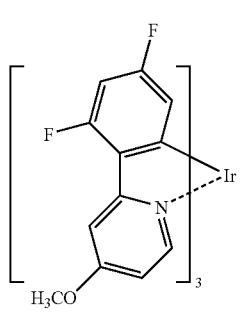
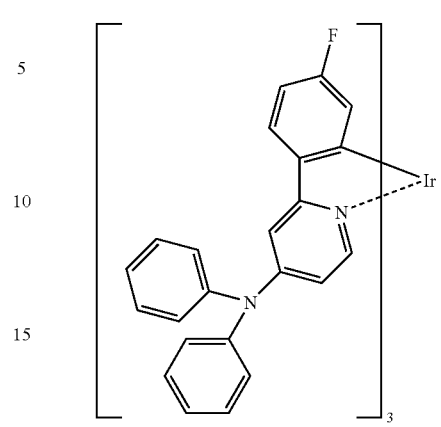
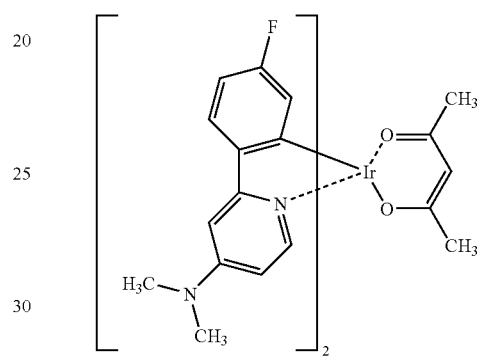
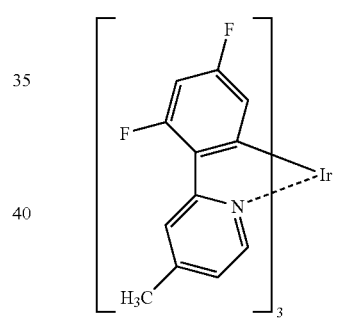
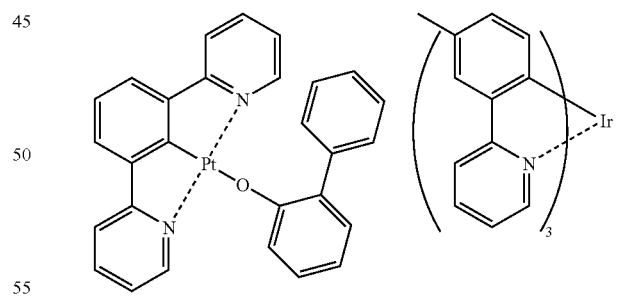
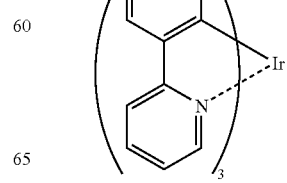

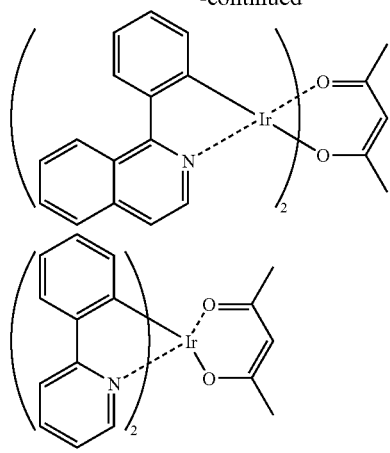

The content of a phosphorescent dopant in an emitting layer is not limited and can be appropriately selected according to purposes; for example, it is 0.1 to 70 mass %, preferably 1 to 30 mass %. When the content of a phosphorescent compound is less than 0.1 mass %, emission may be weak and the advantages thereof may not be sufficiently exhibited. When the content exceeds 70 mass %, the phenomenon called concentration quenching may significantly proceed, thereby degrading the device performance.

As for the fluorescent dopant, it is preferable to select appropriately from an amine-based compound, an aromatic compound, a chelate complex such as a tris(8-quinolilate) aluminum complex, a cumarin derivative, a tetraphenylbutadiene derivative, a bisstyrylarylene derivative, an oxadiazole derivative or the like according to the required emitting color. A styryl amine compound, a styryl diamine compound, an aryl amine compound, and an aryl diamine compound are further preferable. Further, a fused polycyclic aromatic compound which is not an amine compound is preferable. These fluorescent dopants may be used alone or in combination of two or more.

The content of a phosphorescent dopant in an emitting layer is not limited and can be properly selected according to purposes; for example, it is 0.1 to 70 mass %, preferably 1 to 30 mass %.

As the styryl amine compound and the styryl diamine compound, those shown by the following formula (A) are preferable.

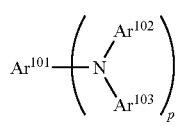
(A)

wherein $Ar^{101}$ is a p-valent group; a valent group corresponding to a phenyl group, a naphthyl group, a biphenyl group, a terphenyl group, a styrylbenzyl group, and distyrylaryl group; $Ar^{102}$ and $Ar^{103}$ are independently an aromatic hydrocarbon group having 6 to 20 carbon atoms, and $Ar^{101}$, $Ar^{102}$ and $Ar^{103}$ may be substituted. Any one of $Ar^{101}$ to $Ar^{103}$ is substituted by a styryl group. Further preferably, at least one of $Ar^{102}$ and $Ar^{103}$ is substituted by a styryl group. p is an integer of 1 to 4, preferably an integer of 1 to 2.

As the aromatic hydrocarbon group having 6 to 20 carbon atoms, a phenyl group, a naphthyl group, an anthranyl group, a phenanthryl group, a terphenyl group or the like can be given.

As the arylamine compound and the aryldiamine compound, those shown by the following formula (B) are preferable.

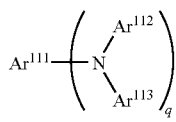
(B)

wherein $Ar^{111}$ is a q-valent substituted or unsubstituted aromatic group having 5 to 40 ring carbon atoms; $Ar^{112}$ and $Ar^{113}$ are independently a substituted or unsubstituted aryl group having 5 to 40 ring carbon atoms; and q is an integer of 1 to 4, preferably an integer of 1 to 2.

Examples of the aryl group having 5 to 40 ring carbon atoms include phenyl, naphthyl, anthranyl, phenanthryl, pyrenyl, coronyl, biphenyl, terphenyl, pyrrolyl, furanyl, thiophenyl, benzothiophenyl, oxadiazolyl, diphenylanthranyl, indolyl, carbazolyl, pyridyl, benzoquinolyl, fluoranthenyl, acetofluoranthenyl, stilbene, perylenyl, chrycenyl, picenyl, triphenylenyl, rubicenyl, benzoanthracenyl, phenylanthranyl and bisanthracenyl, with naphthyl, anthranyl, chrycenyl and pyrenyl being preferable.

As $Ar^{111}$, the above-mentioned q-valent group is preferable. When $Ar^{111}$ is divalent, the group shown by the following formula (C) or (D) is preferable, with the group shown by the formula (D) being preferable.

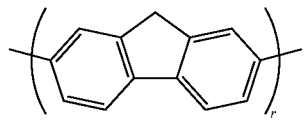
(C)

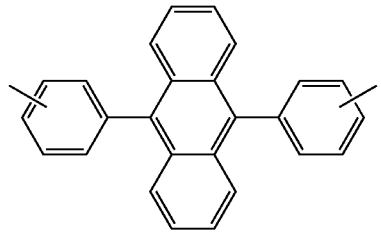
(D)

In the formula (C), r is an integer of 1 to 3.

Examples of the preferred substituent of the above-mentioned aryl group include an alkyl group having 1 to 6 carbon atoms (ethyl, methyl, i-propyl, n-propyl, s-butyl, t-butyl, pentyl, hexyl, cyclopentyl, cyclohexyl, or the like); an alkoxy group having 1 to 6 carbon atoms (ethoxy, methoxy, i-propoxy, n-propoxy, s-butoxy, t-butoxy, pentoxy, hexyloxy, cyclopentoxy, cyclohexyloxy, or the like); an aryl group having 5 to 40 ring carbon atoms; an amino group substituted with an aryl group having 5 to 40 ring carbon atoms; an ester group with an aryl group having 5 to 40 ring carbon atoms; an ester group with an alkyl group having 1 to 6 carbon atoms; a cyano group; a nitro group; and a halogen atom.

The emitting layer may contain hole-transporting materials, electron-transporting materials and polymer binders, if necessary.

The thickness of an emitting layer is preferably from 5 to 50 nm, more preferably from 7 to 50 nm and most preferably from 10 to 50 nm. When it is less than 5 nm, the formation of an emitting layer and the adjustment of chromaticity may become difficult. When it exceeds 50 nm, the driving voltage may increase.

The hole-transporting layer or the hole-injecting layer is a layer for helping the injection of holes into the emitting layer so as to transport holes to an emitting region. These layers have a large hole mobility and usually an ionization energy as small as 5.5 eV or less. Such a hole-injecting or hole-transporting layer is preferably made of a material which can transport holes to the emitting layer at a low electric field intensity. The hole mobility thereof is preferably at least $10^{-4}$ cm$^2$/V·second when an electric field of, e.g. $10^4$ to $10^6$ V/cm is applied.

There are no particular restrictions on the material of the hole-injecting layer and the hole-transporting layer. The material can be arbitrarily selected from materials which have been widely used as a change-transporting material of photoconductive materials and known materials used in a hole-injecting layer or hole-transporting layer of organic EL devices.

For example, an aromatic amine derivative shown by the following formula can be used in the hole-injecting layer and the hole-transporting layer.

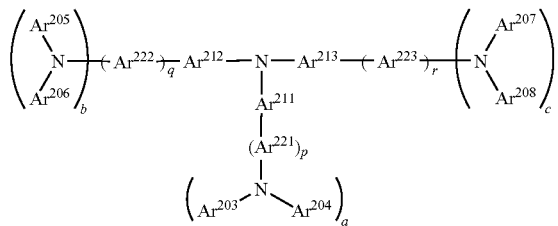

$Ar^{211}$ to $Ar^{213}$, $Ar^{221}$ to $Ar^{223}$ and $Ar^{203}$ to $Ar^{208}$ are independently a substituted or unsubstituted aromatic hydrocarbon group having 6 to 50 ring carbon atoms, or a substituted or unsubstituted aromatic heterocyclic group having 5 to 50 ring atoms. a to c and p to r are each an integer of 0 to 3. $Ar^{203}$ and $Ar^{204}$, $Ar^{205}$ and $Ar^{206}$, and $Ar^{207}$ and $Ar^{208}$ are bonded to each other to form a saturated or unsaturated ring.

Examples of the substituted or unsubstituted aromatic ring group having 6 to 50 ring carbon atoms include a phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, and 4"-t-butyl-p-terphenyl-4-yl group.

Examples of the substituted or unsubstituted aromatic heterocyclic group having 5 to 50 ring atoms include a 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-isoindolyl group, 2-isoindolyl group, 3-isoindolyl group, 4-isoindolyl group, 5-isoindolyl group, 6-isoindolyl group, 7-isoindolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthrolin-2-yl group, 1,7-phenanthrolin-3-yl group, 1,7-phenanthrolin-4-yl group, 1,7-phenanthrolin-5-yl group, 1,7-phenanthrolin-6-yl group, 1,7-phenanthrolin-8-yl group, 1,7-phenanthrolin-9-yl group, 1,7-phenanthrolin-10-yl group, 1,8-phenanthrolin-2-yl group, 1,8-phenanthrolin-3-yl group, 1,8-phenanthrolin-4-yl group, 1,8-phenanthrolin-5-yl group, 1,8-phenanthrolin-6-yl group, 1,8-phenanthrolin-7-yl group, 1,8-phenanthrolin-9-yl group, 1,8-phenanthrolin-10-yl group, 1,9-phenanthrolin-2-yl group, 1,9-phenanthrolin-3-yl group, 1,9-phenanthrolin-4-yl group, 1,9-phenanthrolin-5-yl group, 1,9-phenanthrolin-6-yl group, 1,9-phenanthrolin-7-yl group, 1,9-phenanthrolin-8-yl group, 1,9-phenanthrolin-10-yl group, 1,10-phenanthrolin-2-yl group, 1,10-phenanthrolin-3-yl group, 1,10-phenanthrolin-4-yl group, 1,10-phenanthrolin-5-yl group, 2,9-phenanthrolin-1-yl group, 2,9-phenanthrolin-3-yl group, 2,9-phenanthrolin-4-yl group, 2,9-phenanthrolin-5-yl group, 2,9-phenanthrolin-6-yl group, 2,9-phenanthrolin-7-yl group, 2,9-phenanthrolin-8-yl group, 2,9-phenanthrolin-10-yl group, 2,8-phenanthrolin-1-yl group, 2,8-phenanthrolin-3-yl group, 2,8-phenanthrolin-4-yl group, 2,8-phenanthrolin-5-yl group, 2,8-phenanthrolin-6-yl group, 2,8-phenanthrolin-7-yl group, 2,8-phenanthrolin-9-yl group, 2,8-phenanthrolin-10-yl group, 2,7-phenanthrolin-1-yl group, 2,7-phenanthrolin-3-yl group, 2,7-phenanthrolin-4-yl group, 2,7-phenanthrolin-5-yl group, 2,7-phenanthrolin-6-yl group, 2,7-phenanthrolin-8-yl group, 2,7-phenanthrolin-9-yl group, 2,7-phenanthrolin-10-yl group, 1-phenazinyl group, 2-phenazinyl group, 1-phenothiadinyl group, 2-phenothiadinyl group, 3-phenothiadinyl group, 4-phenothiadinyl group, 10-phenothiadinyl group, 1-phenoxadinyl group, 2-phenoxadinyl group, 3-phenoxadinyl group, 4-phenoxadinyl group, 10-phenoxadinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrol-1-yl group, 2-methylpyrrol-3-yl group, 2-methylpyrrol-4-yl group, 2-methylpyrrol-5-yl group, 3-methylpyrrol-1-yl group, 3-methylpyrrol-2-yl group, 3-methylpyrrol-4-yl group, 3-methylpyrrol-5-yl group, 2-t-butylpyrrol-4-yl group, 3-(2-phenylpropyl)pyrrol-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, and 4-t-butyl-3-indolyl group.

Further, the compounds shown by the following formula can be used in the hole-injecting layer and the hole-transporting layer.

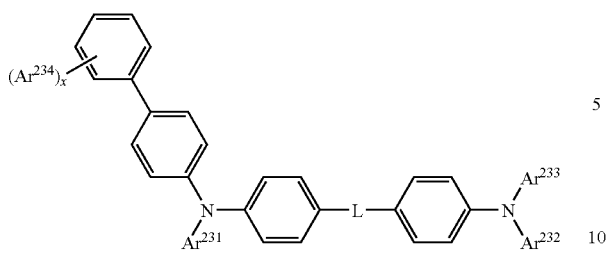

Ar$^{231}$ to Ar$^{234}$ are independently a substituted or unsubstituted aromatic hydrocarbon group having 6 to 50 ring carbon atoms, or a substituted or unsubstituted aromatic heterocyclic group having 5 to 50 ring atoms; L is a linkage group, a single bond, a substituted or unsubstituted aromatic hydrocarbon group having 6 to 50 ring carbon atoms, or a substituted or unsubstituted aromatic heterocyclic group having 5 to 50 ring atoms; and x is an integer of 0 to 5. Ar$^{232}$ and Ar$^{233}$ may be bonded together to form a saturated or unsaturated ring.

As for the specific examples of the substituted or unsubstituted aromatic hydrocarbon group having 6 to 50 ring carbon atoms and a substituted or unsubstituted aromatic heterocyclic group having 5 to 50 ring atoms, the same groups as those exemplified relating to the above-mentioned aromatic amine derivative can be given.

Specific examples of the material for the hole-injecting layer and the hole-transporting layer include a triazole derivative, an oxadiazole derivative, an imidazole derivative, a polyarylalkane derivative, a pyrazoline derivative, a pyrazolone derivative, a phenylenediamine derivative, an arylamine derivative, an amino-substituted chalcone derivative, an oxazole derivative, a styrylanthracene derivative, a fluorenone derivative, a hydrazone derivative, a stilbene derivative, a silazane derivative, an aniline-based copolymer and a conductive high-molecular oligomer (thiophene oligomer, in particular).

The above-mentioned materials can be used as the material for the hole-injecting layer and the hole-transporting layer. It is preferable to use a porphyrin compound, an aromatic tertiary amine compound and a styrylamine compound. It is particularly preferable to use an aromatic tertiary amine compound.

It is preferable to use a compound which has in the molecule thereof two fused aromatic rings, such as 4,4'-bis(N-(1-naphthyl)-N-phenylamino)biphenyl (hereinafter abbreviated as "NPD"), and 4,4',4''-tris(N-(3-methylphenyl)-N-phenylamino)triphenylamine (hereinafter abbreviated as "MTDATA"), wherein three triphenylamine units are linked to each other in a star-burst form.

In addition to these, a nitrogen-containing heterocyclic derivative shown by the following formula can be used.

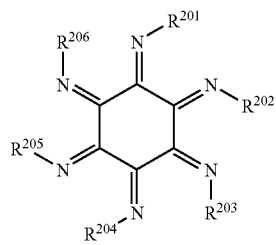

wherein R$^{201}$ to R$^{206}$ are independently any of a substituted or unsubstituted alkyl group, a substituted or unsubstituted aryl group, a substituted or unsubstituted aralkyl group and a substituted or unsubstituted heterocyclic group. R$^{201}$ and R$^{202}$, R$^{203}$ and R$^{204}$, R$^{205}$ and R$^{206}$, R$^{201}$ and R$^{206}$, R$_{202}$ and R$^{203}$, or R$^{204}$ and R$^{205}$ may form a fused ring.

Furthermore, the following compounds may also be used.

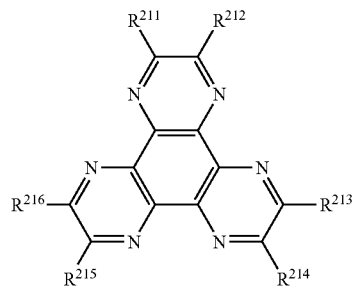

wherein R$^{211}$ to R$^{216}$ are independently a substituent, preferably an electron-attracting group such as a cyano group, a nitro group, a sulfonyl group, a carbonyl group, a trifluoromethyl group or a halogen.

Further, an inorganic compound such as p-type Si and p-type SiC can be used as the material for the hole-injecting layer and the hole-transporting layer.

The hole-transporting layer and hole-transporting layer can be formed as a thin film from the above-mentioned compounds by a known method such as vacuum deposition, spin coating, casting or LB technique. The film thickness of the hole-injecting layer and hole-transporting layer is not particularly limited, and is usually from 5 nm to 5 µm. The hole-injecting layer and hole-transporting layer may be a single layer made of one or two or more of the above-mentioned materials, or may be stacked hole-injecting layers and hole-transporting layers made of different compounds.

The organic semiconductor layer is a layer for helping the injection of holes or electrons into the emitting layer, and is preferably a layer having an electric conductivity of 10$^{-10}$ S/cm or more. As the material of such an organic semiconductor layer, electroconductive oligomers such as thiophene-containing oligomers or arylamine-containing oligomers and electroconductive dendrimers such as arylamine-containing dendrimers may be used.

The electron-injecting layer and the electron-transporting layer are each a layer which assists injection of electrons into the emitting layer and transports electrons to the emitting region, and exhibits a high electron mobility. The adhesion-improvement layer is a kind of the electron-injecting layer which is composed of a material which exhibits good adhesion to the cathode.

The thickness of the electron-transporting layer is arbitrarily selected in the range of 5 nm to 5 µm. When the electron-transporting layer has a large thickness, it is preferable that the electron mobility be 10$^{-5}$ cm$^2$/Vs or more at an applied electric field of 10$^4$ to 10$^6$ V/cm in order to prevent an increase in voltage.

The material used in the electron-injecting layer and electron-transporting layer is preferably a metal complex of 8-hydroxyquinoline or a derivative thereof, or an oxadiazole derivative. Specific examples of the metal complexes of 8-hydroxyquinoline or derivatives thereof include metal chelate oxynoid compounds containing a chelate of oxine (generally, 8-quinolinol or 8-hydroxyquinoline) such as tris(8-quinolinolato)aluminum.

An electron-transporting compound of the following formula can be given as the oxadiazole derivative.

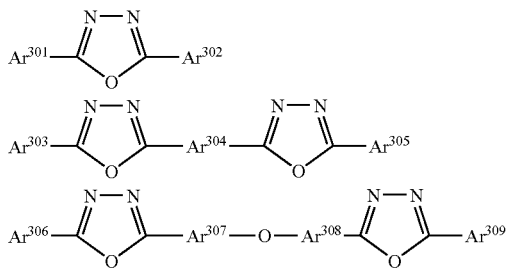

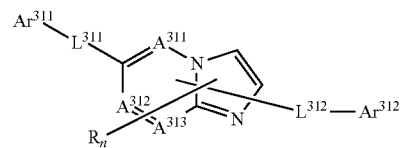

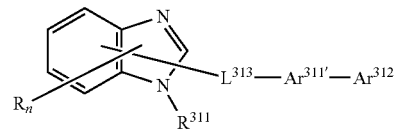

wherein $Ar^{301}$, $Ar^{302}$, $Ar^{303}$, $Ar^{305}$, $Ar^{306}$ and $Ar^{309}$ are independently substituted or unsubstituted aryl groups; and $Ar^{304}$, $Ar^{307}$ and $Ar^{308}$ are independently substituted or unsubstituted arylene groups.

As examples of the aryl group, a phenyl group, a biphenyl group, an anthranyl group, a perylenyl group, and a pyrenyl group can be given. As examples of the arylene group, a phenylene group, a naphthylene group, a biphenylene group, an anthranylene group, a perylenylene group, a pyrenylene group, and the like can be given. As the substituent, an alkyl group having 1 to 10 carbon atoms, an alkoxy group having 1 to 10 carbon atoms, a cyano group, and the like can be given. The electron-transporting compound is preferably one from which a thin film can be formed.

The following compounds can be given as specific examples of the electron-transporting compound.

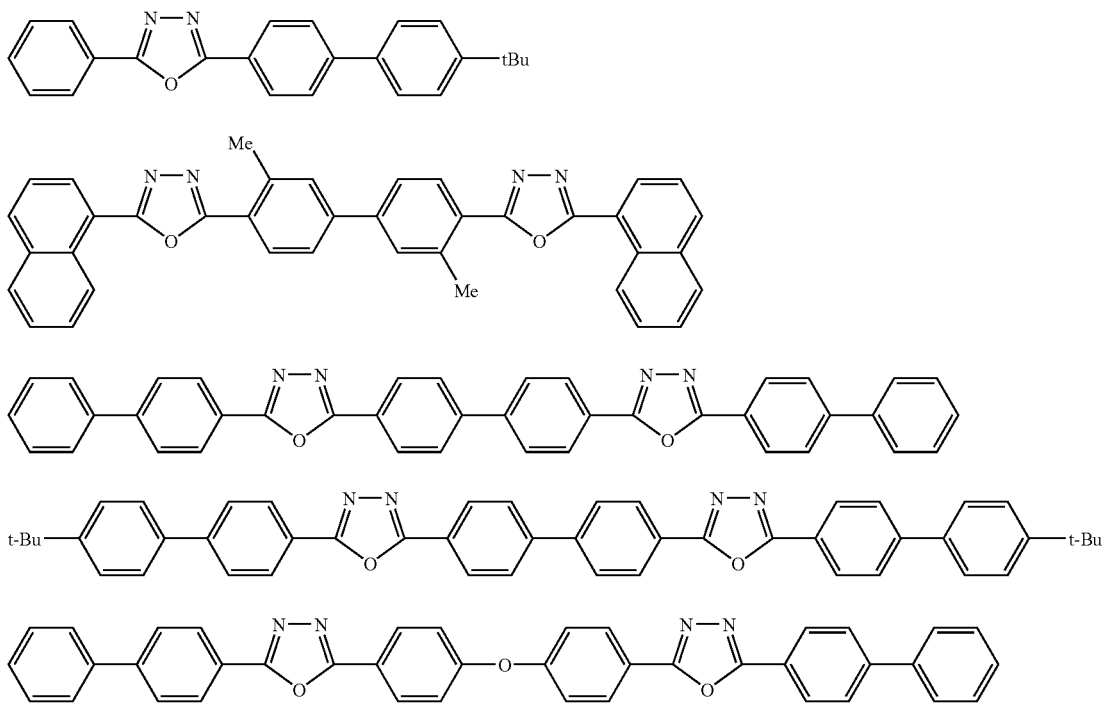

(Me indicates a methyl group and tBu indicates a t-butyl group.)

Furthermore, as materials used for the electron-injecting layer and electron-transporting layer, the compounds represented by the following formulas (E) to (J) may be used.

Nitrogen-containing heterocyclic derivatives shown by the above formulas (E) and (F), wherein $A^{311}$ to $A^{313}$ are independently a nitrogen atom or a carbon atom;

$Ar^{311}$ is a substituted or unsubstituted aryl group having 6 to 60 ring carbon atoms or a substituted or unsubstituted heteroaryl group having 3 to 60 ring atoms; $Ar^{311'}$ is a substituted or unsubstituted arylene group having 6 to 60 ring carbon atoms or a substituted or unsubstituted heteroarylene group having 3 to 60 ring atoms; $Ar^{312}$ is a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms, or a substituted or unsubstituted alkoxy group having 1 to 20 carbon atoms, provided that one of $Ar^{311}$ and $Ar^{312}$ is a substituted or unsubstituted fused ring group having 10 to 60 ring carbon atoms or a substituted or unsubstituted mono-heterofused ring group having 3 to 60 ring atoms;

$L^{311}$, $L^{312}$ and $L^{313}$ are independently a single bond, a substituted or unsubstituted arylene group having 6 to 60 ring carbon atoms, a substituted or unsubstituted heteroarylene group having 3 to 60 ring atoms or a substituted or unsubstituted fluorenylene group;

R and $R^{311}$ are independently a hydrogen atom, a substituted or unsubstituted aryl group having 6 to 60 ring carbon atoms, a substituted or unsubstituted heteroaryl group having 3 to 60 ring atoms, a substituted or unsubstituted alkyl group having 1 to 20 carbon atoms, or a substituted or unsubstituted alkoxy group having 1 to 20 carbon atoms, and n is an integer of 0 to 5, provided that, when n is an integer of 2 or more, a plurality of Rs may be the same or different; and adjacent Rs may be bonded to form a carbocyclic aliphatic ring or a carbocyclic aromatic ring.

$$HAr\text{-}L^{314}\text{-}Ar^{32}\text{—}Ar^{322} \tag{G}$$

Nitrogen-containing heterocyclic derivatives shown by the above formula (G) wherein HAr is a nitrogen-containing heterocyclic ring with 3 to 40 carbon atoms which may have a substituent; $L^{314}$ is a single bond, an arylene group with 6 to 60 carbon atoms which may have a substituent, a heteroarylene group with 3 to 60 carbon atoms which may have a substituent or a fluorenylene group which may have a substituent; $Ar^{321}$ is a divalent aromatic hydrocarbon group with 6 to 60 atoms which may have a substituent; and $Ar^{322}$ is an aryl group with 6 to 60 carbon atoms which may have a substituent or a heteroaryl group with 3 to 60 atoms which may have a substituent.

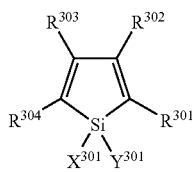
(H)

Silacyclopentadiene derivatives represented by the formula (H) wherein $X^{301}$ and $Y^{301}$ are independently a saturated or unsaturated hydrocarbon group having 1 to 6 carbon atoms, an alkoxy group, an alkenyloxy group, an alkynyloxy group, a hydroxy group, a substituted or unsubstituted aryl group, or a substituted or unsubstituted hetero ring, or X and Y are bonded to form a saturated or unsaturated ring, and $R^{301}$ to $R^{304}$ are independently hydrogen, halogen, an alkyl group, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a heterocyclic group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group; these groups may be substituted, or adjacent groups may form a substituted or unsubstituted fused ring.

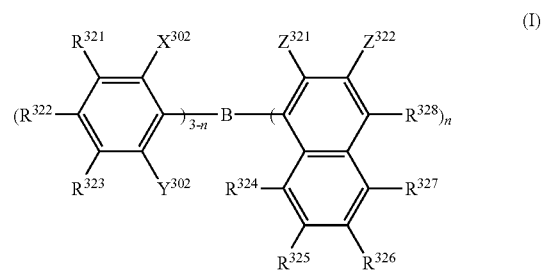

Borane derivatives shown by the formula (I) wherein $R^{321}$ to $R^{328}$ and $Z^{322}$ are independently a hydrogen atom, a saturated or unsaturated hydrocarbon group, an aromatic hydrocarbon group, a heterocyclic group, a substituted amino group, a substituted boryl group, an alkoxy group, or an aryloxy group, $X^{302}$, $Y^{302}$, and $Z^{321}$ are independently a saturated or unsaturated hydrocarbon group, an aromatic hydrocarbon group, a heterocyclic group, a substituted amino group, an alkoxy group, or an aryloxy group, $Z^{321}$ and $Z^{322}$ may be bonded to form a fused ring, n is an integer of 1 to 3 and when n or (3−n) is 2 or more, $R^{321}$ to $R^{328}$, $X^{302}$, $Y^{302}$, $Z^{322}$ and $Z^{321}$ may be the same or different, provided that a compound in which n is 1, X, Y, and $R^{322}$ are methyl groups, and $R^{328}$ is a hydrogen atom or a substituted boryl group, and a compound in which n is 3 and $Z^{321}$ is a methyl group are excluded.

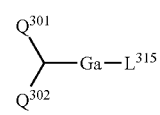
(J)

Gallium complexes shown by the following formula (J) wherein $Q^{301}$ and $Q^{302}$ are independently ligands represented by the following formula (K) and $L^{315}$ is a halogen atom, a substituted or unsubstituted alkyl group, a substituted or unsubstituted cycloalkyl group, a substituted or unsubstituted aryl group, a substituted or unsubstituted heterocyclic group, —OR(R is a hydrogen atom, a substituted or unsubstituted alkyl group, a substituted or unsubstituted cycloalkyl group, a substituted or unsubstituted aryl group, or a substituted or unsubstituted heterocyclic group) or a ligand represented by —O—Ga-$Q^{303}$($Q^{304}$)($Q^{303}$ and $Q^{304}$ have the same meanings as $Q^{301}$ and $Q^{302}$).

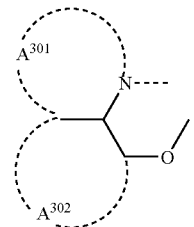
(K)

wherein rings $A^{301}$ and $A^{302}$ are independently a 6-membered aryl ring structure which may have a substituent, and are fused to each other.

The metal complexes have the strong nature of an n-type semiconductor and large ability of injecting electrons. Further, the energy generated at the time of forming a complex is small so that a metal is then strongly bonded to ligands in the metal complex formed and the fluorescent quantum efficiency is large as the emitting material.

Specific examples of the substituents for the rings $A^{301}$ and $A^{302}$ forming the ligand of the formula (K) include halogen atoms such as chlorine, bromine, iodine, and fluorine, substituted or unsubstituted alkyl groups such as a methyl group, ethyl group, propyl group, butyl group, sec-butyl group, tert-butyl group, pentyl group, hexyl group, heptyl group, octyl group, stearyl group, and trichloromethyl group, substituted or unsubstituted aryl groups such as a phenyl group, naphthyl group, biphenyl group, anthranyl group, phenanthryl group, fluorenyl group, pyrenyl group, 3-methylphenyl group, 3-methoxyphenyl group, 3-fluorophenyl group, 3-trichloromethylphenyl group, 3-trifluoromethylphenyl group, and 3-nitrophenyl group, substituted or unsubstituted alkoxy groups such as a methoxy group, n-butoxy group, tert-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, and 6-(perfluoroethyl)hexyloxy group, substituted or unsubstituted aryloxy groups such as a phenoxy group, p-nitrophenoxy group, p-tert-butylphenoxy group, 3-fluorophenoxy group, pentafluorophenyl group, and 3-trifluoromethylphenoxy group, substituted or unsubstituted alkylthio groups such as a methylthio group, ethylthio group, tert-butylthio group, hexylthio group, octylthio group, and trifluoromethylthio group, substituted or unsubstituted arylthio groups such as a phenylthio group, p-nitrophenylthio group, p-tert-butylphenylthio group, 3-fluorophenylthio group, pentafluorophenylthio group, and 3-trifluoromethylphenylthio group, a cyano group, a nitro group, an amino group, mono- or di-substituted amino groups such as a methylamino group, diethylamino group, ethylamino group, diethylamino group, dipropylamino group, dibutylamino group, and diphenylamino group, acylamino groups such as a bis(acetoxymethyl)amino group, bis(acetoxyethyl)amino group, bis(acetoxypropyl) amino group, and bis(acetoxybutyl)amino group, a hydroxy group, a siloxy group, an acyl group, substituted or unsubstituted carbamoyl groups such as a carbomoyl group, methylcarbamoyl group, dimethylcarbamoyl group, ethylcarbamoyl group, diethylcarbamoyl group, propylcarbamoyl group, butylcarbamoyl group, and phenylcarbamoyl group, a carboxylic acid group, a sulfonic acid group, an imide group, cycloalkyl groups such as a cyclopentane group and a cyclohexyl group, heterocyclic groups such as a pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, carbazolyl group, furanyl group, thiophenyl group, oxazolyl group, oxadiazolyl group, benzooxazolyl group, thiazolyl group, thiadiazolyl group, benzothiazolyl group, triazolyl group, imidazolyl group, and benzimidazolyl group. The above substituents may be bonded to form a six-membered aryl ring or heterocyclic ring.

In a preferred embodiment of the organic EL device, a reducing dopant is contained in an electron-transferring region or in an interfacial region between the cathode and the organic layer. The reducing dopant is defined as a substance which can reduce an electron-transferring compound. Accordingly, various substances which have given reducing properties can be used. For example, at least one substance can be preferably used which is selected from the group consisting of alkali metals, alkaline earth metals, rare earth metals, alkali metal oxides, alkali metal halides, alkaline earth metal oxides, alkaline earth metal halides, rare earth metal oxides, rare earth metal halides, alkali metal carbonates, alkaline earth metal carbonates, rare metal carbonates, alkali metal organic complexes, alkaline earth metal organic complexes, and rare earth metal organic complexes.

More specific examples of the preferred reducing dopants include at least one alkali metal selected from the group consisting of Na (work function: 2.36 eV), K (work function: 2.28 eV), Rb (work function: 2.16 eV) and Cs (work function: 1.95 eV), and at least one alkaline earth metal selected from the group consisting of Ca (work function: 2.9 eV), Sr (work function: 2.0 to 2.5 eV), and Ba (work function: 2.52 eV). Metals having a work function of 2.9 eV or less are particularly preferred. A reducing dopant having a work function of 2.9 eV or less is particularly preferable. Among these, a more preferable reducing dopant is at least one alkali metal selected from the group consisting of K, Rb and Cs. Even more preferable is Rb or Cs. Most preferable is Cs. These alkali metals are particularly high in reducing ability. Thus, the addition of a relatively small amount thereof to an electron-injecting zone improves the luminance of the organic EL device and make the lifetime thereof long. As a reducing agent having a work function of 2.9 eV or less, combinations of two or more alkali metals are preferable, particularly combinations including Cs, such as Cs and Na, Cs and K, Cs and Rb, or Cs, Na and K are preferable. The combination containing Cs makes it possible to exhibit the reducing ability efficiently. The luminance of the organic EL device can be improved and the lifetime thereof can be made long by the addition thereof to its electron-injecting zone.

In the invention, an electron-injecting layer made of an insulator or a semiconductor may further be provided between a cathode and an organic layer. By forming the electron-injecting layer, a current leakage can be effectively prevented and electron-injecting properties can be improved. When the electron-injecting layer is formed of insulating thin films, more uniformed thin film is formed whereby pixel defects such as a dark spot are decreased.

As the insulator, at least one metal compound selected from the group consisting of alkali metal calcogenides, alkaline earth metal calcogenides, halides of alkali metals and halides of alkaline earth metals can be preferably used. When the electron-injecting layer is formed of the alkali metal calcogenide or the like, the injection of electrons can be preferably further improved. Specifically preferable alkali metal calcogenides include $Li_2O$, $K_2O$, $Na_2S$, $Na_2Se$ and $Na_2O$ and preferable alkaline earth metal calcogenides include CaO, BaO, SrO, BeO, BaS and CaSe. Preferable halides of alkali metals include LiF, NaF, KF, CsF, LiCl, KCl and NaCl. Preferable halides of alkaline earth metals include fluorides such as $CaF_2$, $BaF_2$, $SrF_2$, $MgF_2$ and $BeF_2$ and halides other than fluorides.

Semiconductors forming an electron-injecting layer include one or combinations of two or more of oxides, nitrides, and oxidized nitrides containing at least one element of Ba, Ca, Sr, Yb, Al, Ga, In, Li, Na, Cd, Mg, Si, Ta, Sb and Zn. An inorganic compound forming an electron-injecting layer is preferably a microcrystalline or amorphous insulating thin film.

For the cathode, the following may be used: an electrode substance made of a metal, an alloy or an electroconductive compound, or a mixture thereof which has a small work function (for example, 4 eV or less). Specific examples of the electrode substance include sodium, sodium-potassium alloy, magnesium, lithium, cesium, magnesium/silver alloy, aluminum/aluminum oxide, $Al/Li_2O$, Al/LiO, Al/LiF, aluminum/lithium alloy, indium, and rare earth metals.

The cathode can be prepared from these electrode materials by vapor deposition, sputtering or the like.

In the case where emission from the emitting layer is outcoupled through the cathode, it is preferred to make the transmittance of the cathode to the emission larger than 10%. The sheet resistance of the cathode is preferably several hundreds Ω/□ or less, and the film thickness thereof is usually from 10 nm to 1 μm, preferably from 50 to 200 nm.

In the organic EL device, pixel defects based on leakage or a short circuit are easily generated since an electric field is applied to the super thin film. In order to prevent this, it is preferred to insert an insulative thin layer between the pair of electrodes.

Examples of the material used in the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or laminate thereof may be used.

As for the method for fabricating an organic EL device, for example, necessary layers are sequentially formed from the anode by using the materials and methods mentioned above, and a cathode is finally formed. The organic EL device can be fabricated in the order reverse to the above, i.e., the order from a cathode to an anode.

An example of the fabrication of the organic EL device will be described below which has a structure wherein the following are sequentially formed on a transparent substrate: anode/ hole-injecting layer/emitting layer/electron-injecting layer/ cathode.

First, on a transparent substrate, a thin film formed of an anode material is formed by a vapor deposition method or a sputtering method to form an anode. Next, a hole-injecting layer is formed on this anode. As described above, the hole-injecting layer can be formed by vacuum deposition, spin coating, casting, LB technique, or some other method. Vacuum deposition is preferred since a homogenous film is easily obtained and pinholes are not easily generated. In the case where the hole-injecting layer is formed by vacuum deposition, conditions for the deposition vary depending upon a compound used (a material for the hole-injecting layer), a desired structure of the hole-injecting layer, and others. In general, the conditions are preferably selected from the following: deposition source temperature of 50 to 450° C., vacuum degree of $10^{-7}$ to $10^{-3}$ Torr, vapor deposition rate of 0.01 to 50 nm/second, and substrate temperature of −50 to 300° C.

Next, an emitting layer is formed on the hole-injecting layer. The emitting layer can also be formed by making an emitting material into a thin film by vacuum vapor deposition, sputtering, spin coating, casting or some other method. Vacuum vapor deposition is preferred since a homogenous film is easily obtained and pinholes are not easily generated. In the case where the emitting layer is formed by vacuum vapor deposition, conditions for the deposition, which vary depending on a compound used, can be generally selected from conditions similar to those for the hole-injecting layer.

Next, an electron-injecting layer is formed on the emitting layer. Like the hole-injecting layer and the emitting layer, the layer is preferably formed by vacuum vapor deposition because a homogenous film is required. Conditions for the deposition can be selected from conditions similar to those for the hole-injecting layer and the emitting layer.

Lastly, a cathode is stacked thereon to obtain an organic EL device. A cathode can be formed by a vapor deposition method or sputtering. However, vapor vacuum deposition is preferred in order to protect underlying organic layers from being damaged when the cathode film is formed.

For the organic EL device fabrication that has been described above, it is preferred that the formation from the anode to the cathode is continuously carried out, using only one vacuuming operation.

The method for forming each of the layers in the organic EL device of the invention is not particularly limited. The organic thin film layers containing the compound of this invention can be formed by a known method such as vacuum vapor deposition, molecular beam epitaxy (MBE), or an applying coating method using a solution in which the compound of the invention is dissolved in a solvent, such as dipping, spin coating, casting, bar coating, or roll coating.

EXAMPLES

Synthesis of a Chrysene Derivative

Example 1

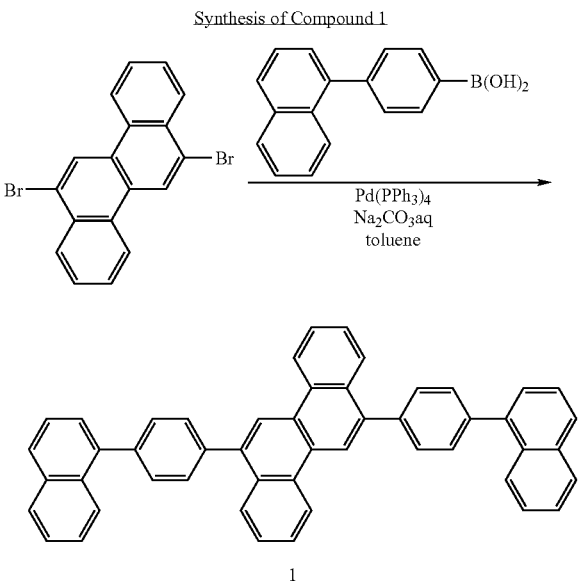

In an argon atmosphere, 80 mL of toluene and 40 mL of a 2M sodium carbonate aqueous solution were added to 3.83 g (10.0 mmol) of 6,12-dibromochrysene, 5.95 g (24.0 mmol) of 4-(1-naphthyl)phenylboronic acid and 0.462 g (0.400 mmol) of tetraxis(triphenylphosphine)palladium(0), followed by heating under reflux for 16 hours. After the completion of the reaction, deposited crystals were filtered out, and the thus obtained crystals were washed with water, methanol and hexane. The resulting solids were recrystallized with toluene, whereby 5.06 g of white crystals were obtained. As a result of a mass spectroscopic analysis, the resulting white crystals were found to be an intended product, and had an m/e value of 632 relative to the molecular weight of 632.25.

Example 2

Synthesis of Compound 2

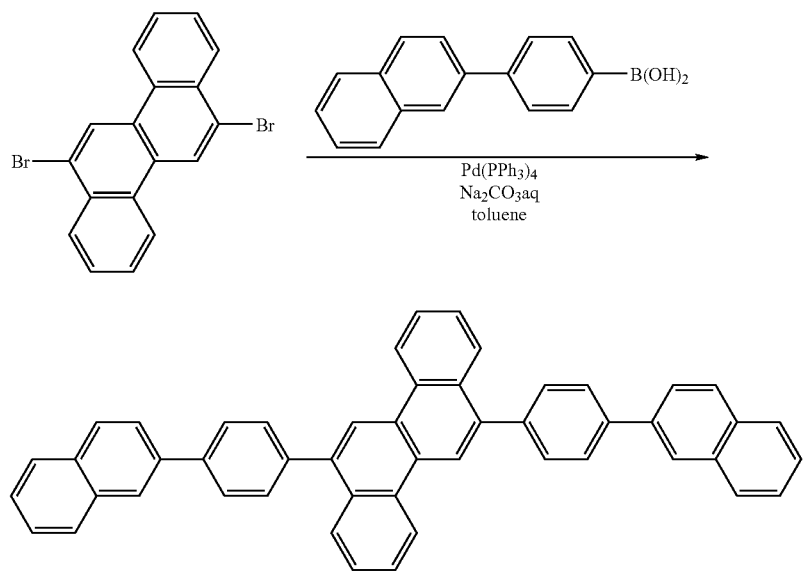

A compound was synthesized in substantially the same manner as in Example 1, except that 4-(2-naphthyl)phenylboronic acid was used instead of 4-(1-naphthyl)phenylboronic acid. As a result of a mass spectroscopic analysis, the resulting compound was found to be an intended product, and had an m/e value of 632 relative to the molecular weight of 632.25

Example 3

Synthesis of Compound 3

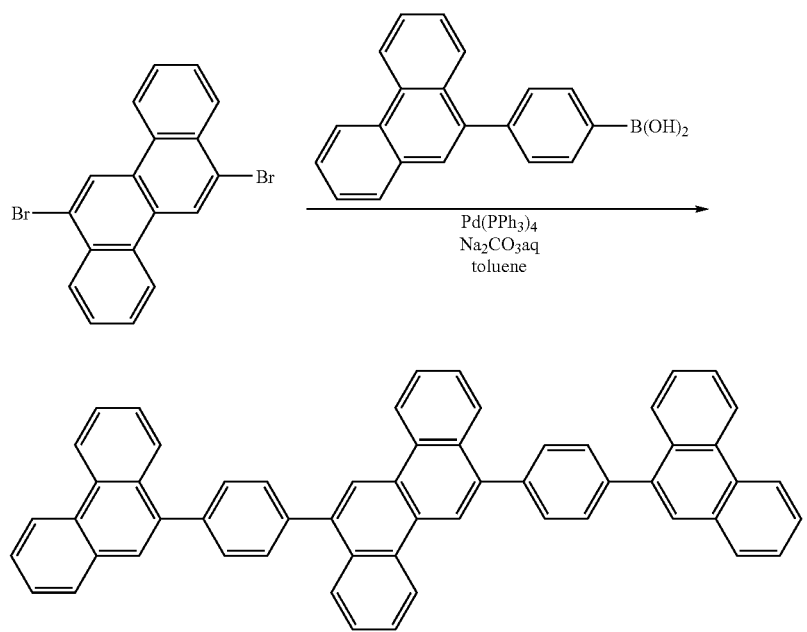

A compound was synthesized in substantially the same manner as in Example 1, except that 4-(9-phenanthryl)phenylboronic acid was used instead of 4-(1-naphthyl)phenylboronic acid. As a result of a mass spectroscopic analysis, the resulting compound was found to be an intended product, and had an m/e value of 732 relative to the molecular weight of 732.28.

Example 4

Synthesis of Compound 4

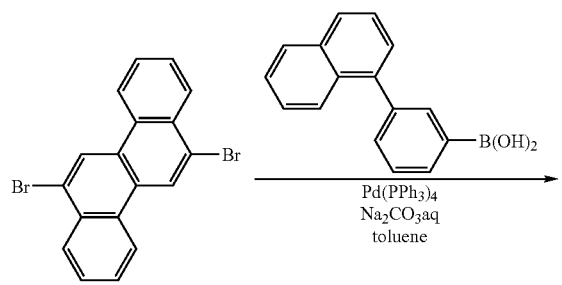

4

A compound was synthesized in substantially the same manner as in Example 1, except that 3-(1-naphthyl)phenylboronic acid was used instead of 4-(1-naphthyl)phenylboronic acid. As a result of a mass spectroscopic analysis, the resulting compound was found to be an intended product, and had an m/e value of 632 relative to the molecular weight of 632.25.

Example 5

Synthesis of Compound 5

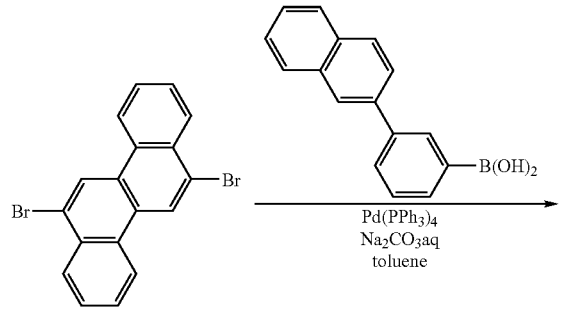

-continued

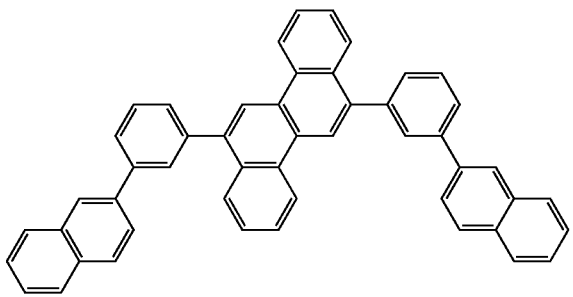

5

A compound was synthesized in substantially the same manner as in Example 1, except that 3-(2-naphthyl)phenylboronic acid was used instead of 4-(1-naphthyl)phenylboronic acid. As a result of a mass spectroscopic analysis, the resulting compound was found to be an intended product, and had an m/e value of 632 relative to the molecular weight of 632.25.

Example 6

Synthesis of Compound 6

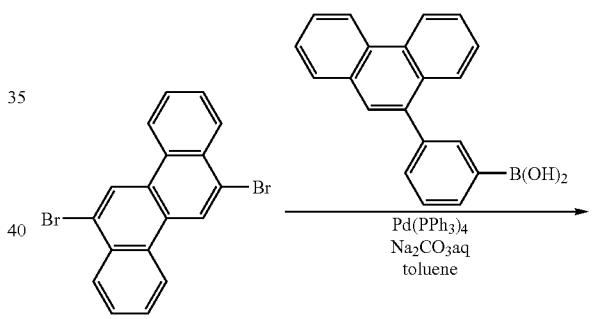

6

A compound was synthesized in substantially the same manner as in Example 1, except that 3-(9-phenanthryl)phenylboronic acid was used instead of 4-(1-naphthyl)phenylboronic acid. As a result of a mass spectroscopic analysis, the resulting compound was found to be an intended product, and had an m/e value of 732 relative to the molecular weight of 732.28.

Example 7

Synthesis of Compound 7

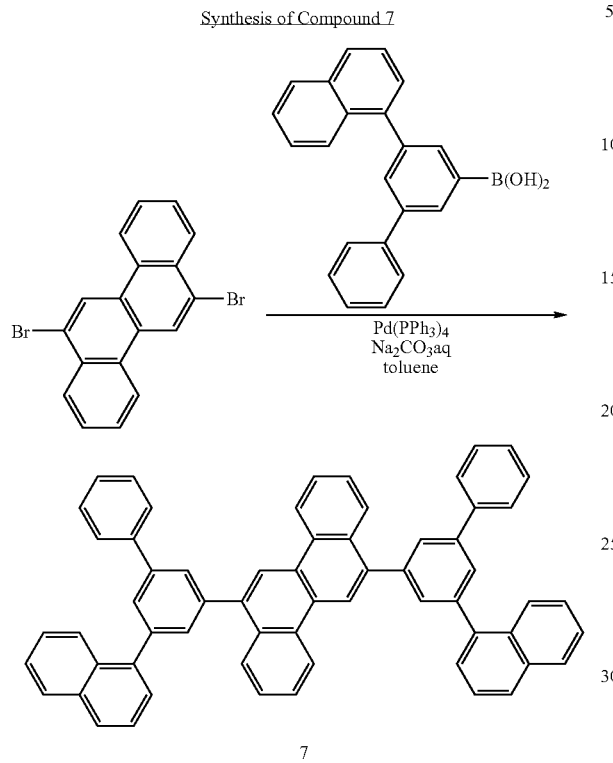

A compound was synthesized in substantially the same manner as in Example 1, except that 3-(1-naphthyl)-5-phenylboronic acid was used instead of 4-(1-naphthyl)phenylboronic acid. As a result of a mass spectroscopic analysis, the resulting compound was found to be an intended product, and had an m/e value of 784 relative to the molecular weight of 784.31.

Example 8

Synthesis of Compound 8

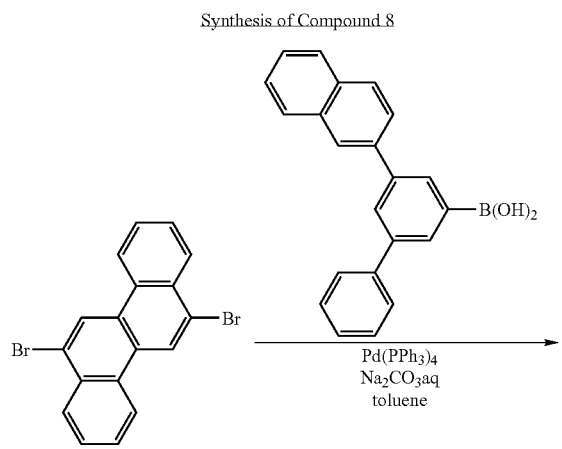

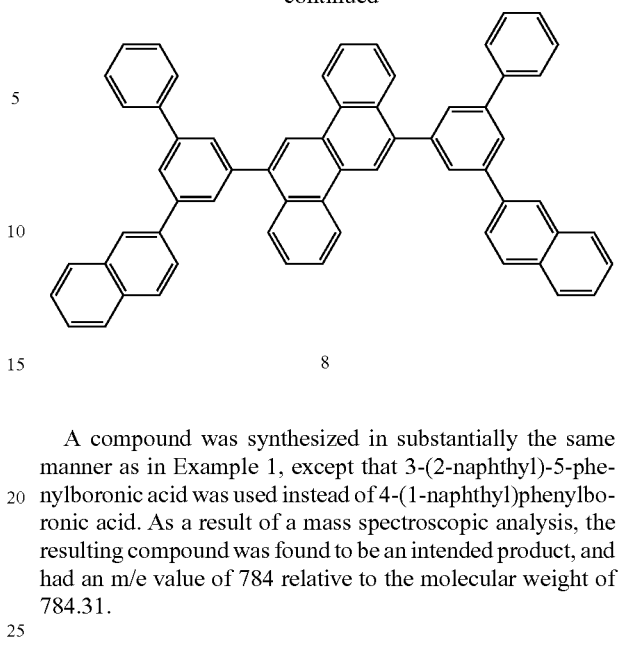

A compound was synthesized in substantially the same manner as in Example 1, except that 3-(2-naphthyl)-5-phenylboronic acid was used instead of 4-(1-naphthyl)phenylboronic acid. As a result of a mass spectroscopic analysis, the resulting compound was found to be an intended product, and had an m/e value of 784 relative to the molecular weight of 784.31.

Example 9

Synthesis of Compound 9

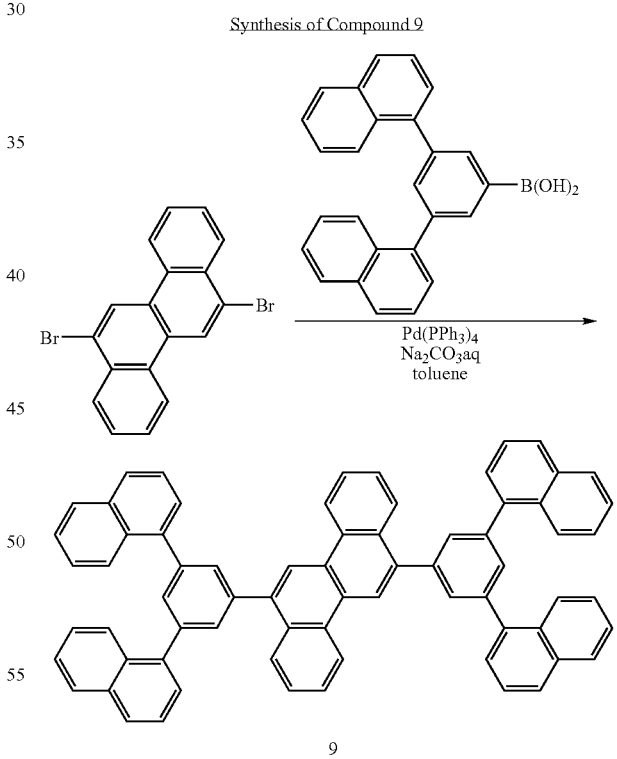

A compound was synthesized in substantially the same manner as in Example 1, except that 3,5-di(1-naphthyl)phenylboronic acid was used instead of 4-(1-naphthyl)phenylboronic acid. As a result of a mass spectroscopic analysis, the resulting compound was found to be an intended product, and had an m/e value of 884 relative to the molecular weight of 884.34.

Example 10

Synthesis of Compound 10

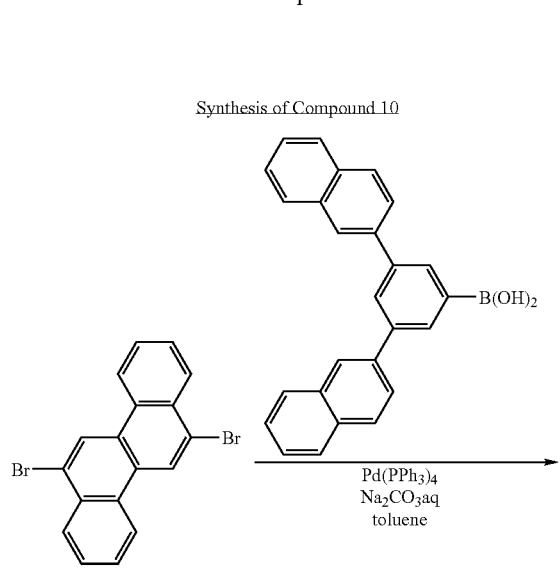

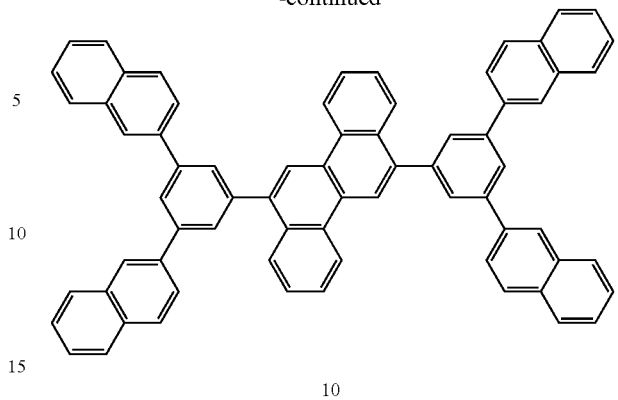

A compound was synthesized in substantially the same manner as in Example 1, except that 3,5-di(2-naphthyl)phenylboronic acid was used instead of 4-(1-naphthyl)phenylboronic acid. As a result of a mass spectroscopic analysis, the resulting compound was found to be an intended product, and had an m/e value of 884 relative to the molecular weight of 884.34.

Example 11

Synthesis of Compound 11

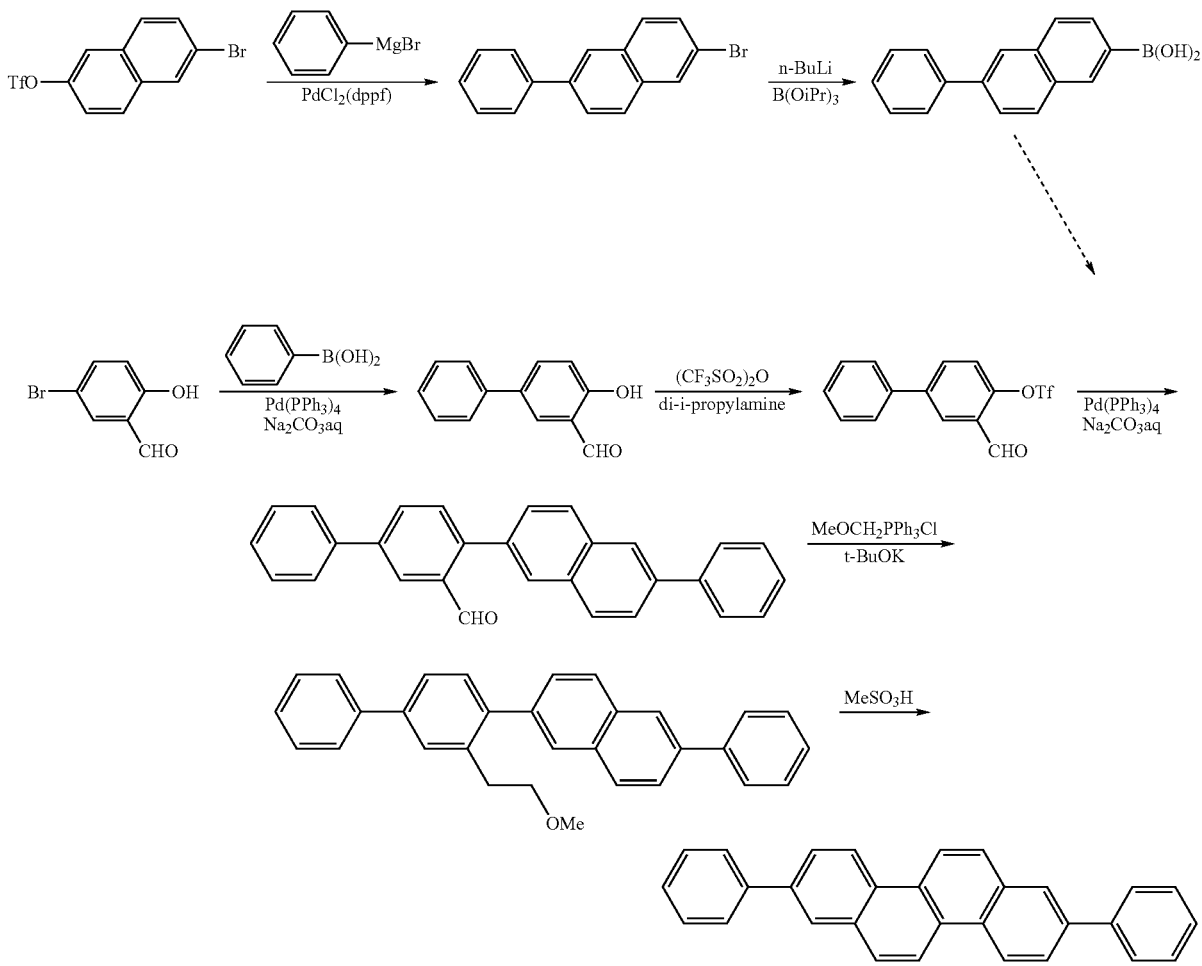

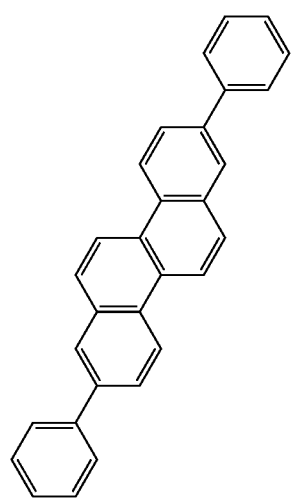
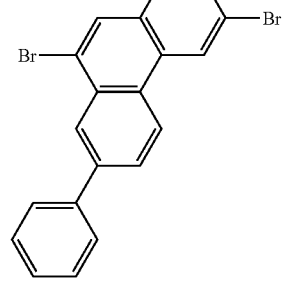
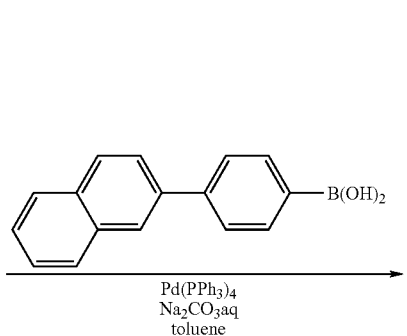
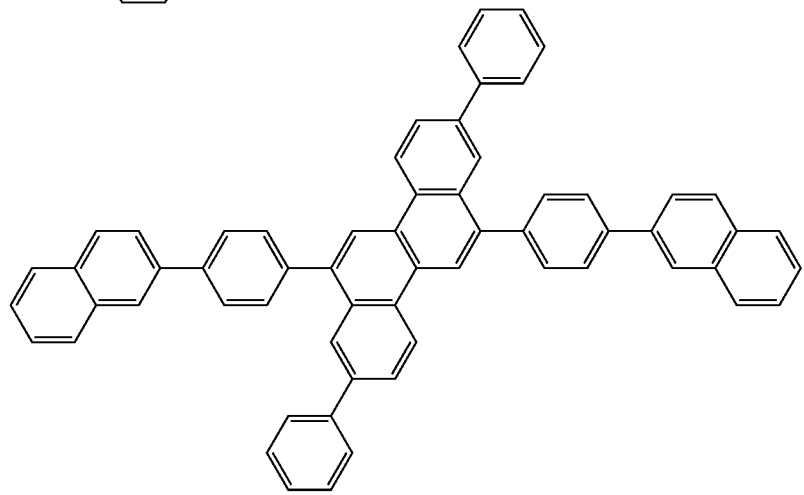

11

(11-1) Synthesis of 2-bromo-6-phenylnaphthalene

In an atmosphere of argon, 1195 g (3.37 mol) of 6-bromo-2-naphthyltrifluoromethane sulfonate, 99.3 g (168 mmol) of 1,3-bis(diphenylphosphino)propane palladium(0)dichloride and 4 L of dehydrated diethyl ether were charged in a flask and cooled to 0° C. Then, 4.1 L of a THF (tetrahydroxyfuran) solution of 1M phenyl magnesium bromide was added dropwise, and stirred at room temperature for 22 hours. After adding 2 L of toluene and 2 L of water, the resulting mixture was filtered. An organic layer of the filtrate was dried with magnesium sulfate, and the solvent was distilled off under a reduced pressure. The residues were subjected to slurry washing and crystals were filtered out. The crystals were dried under a reduced pressure to obtain 360 g of 2-bromo-6-phenylnaphthalene (yield: 38%).

(11-2) Synthesis of 6-phenylnaphthalene-2-boronic acid

In an atmosphere of argon, 360 g (1.27 mol) of 2-bromo-6-phenylnaphthalene, 2 L of dehydrated diethyl ether and 2 L of dehydrated toluene were charged and cooled to −10° C. Then, 1 L (1.58 mol) of a hexane solution of 1.58M n-butyl lithium was added dropwise, and stirred at −10° C. for 5 hours. The reaction solution was cooled to −60° C., and after adding 718 g (3.81 mol) of triisopropyl borate, the mixture was stirred at room temperature for 17 hours. After adding 1 L of toluene and 1 L of water, the resulting mixture was stirred for an hour. Then, an aqueous layer was removed. An organic layer was washed with water, and dried with magnesium sulfate. The organic layer was concentrated, and heat-washed with toluene, whereby 276 g of 6-phenylnaphthalene-2-boronic acid was obtained (yield: 87%).

(11-3) Synthesis of 3-formyl-4-hydroxyphenyl

In an atmosphere of argon, 496 g (2.46 mol) of 5-bromo-salicylaldehyde, 361 g (2.96 mol) of phenylboronic acid, 57 g (49.0 mmol) of tetraxis(triphenylphosphine)palladium(0), 8.6 L of DME and 784 g of sodium carbonate/3.7 L of water were charged, and subjected to heating under reflux with stirring for 17 hours. After cooling the resultant to room temperature, 3 L of toluene was added, and then an aqueous layer was removed. An organic layer was washed with water, and dried with magnesium sulfate. The solvent was distilled off under a reduced pressure. The crystals were purified by silica gel chromatography, whereby 382 g of 3-formyl-4-hydroxybiphenyl was obtained (yield: 78%).

(11-4) Synthesis of 3-formyl-4-biphenyltrifluoromethane sulfonate

In an atmosphere of argon, 382 g (1.93 mol) of 3-formyl-4-hydroxybiphenyl, 390 g (3.85 mol) of diisopropylamine, 4 L of dehydrated dichloromethane were charged. Then, 1088 g (3.85 mol) of trifluoromethanesulfonic anhydride was added dropwise, and the resultant was stirred for 21 hours at room temperature. After adding 100 g of sodium hydrogen carbonate/3 L of water, an aqueous layer was removed.

An organic layer was washed with water, and dried with magnesium sulfate. The solvent was distilled off under a reduced pressure. The crystals were purified by silica gel chromatography, whereby 656 g of a crude product of 3-formyl-4-biphenyltrifluoromethane sulfonate was obtained.

(11-5) Synthesis of 2-(3-formylbiphenyl-4-yl)-6-phenylnaphthalene

In an argon atmosphere, 444 g (1.11 mol) of 3-formyl-4-biphenyltrifluoromethanesulfonate, 276 g (1.33 mol) of phenylboronic acid, 26 g (22.2 mmol) of tetraxis(triphenylphosphine)palladium(0), 5 L of toluene and 354 g of sodium carbonate/1.7 L of water were charged, and subjected to heating under reflux with stirring for 17 hours. After cooling to room temperature, an aqueous layer was removed and an organic layer was washed with water. After drying with magnesium sulfate, the solvent was distilled off under a reduced pressure. The resultant was washed with toluene-acetone, whereby 370 g of 2-(3-formylbiphenyl-4-yl)-6-phenylnaphthalene was obtained (yield: 86%).

(11-6) Synthesis of 2-[3-[2-methoxy]ethenyl-1-yl]biphenyl-4-yl]-6-phenylnaphtalene In an atmosphere of argon, 823 g (2.40 mol) of (methoxymethyl)triphenylphosphonium chloride and 4 L of dehydrated diethyl ether were charged in a flask. Then, 2.4 L (2.40 mol) of a THF solution of 1M potassium-t-butoxide was added, and the resultant was stirred for 2 hours at room temperature. Then, 6 L of a THF dispersion of 370 g (961 mmol) of 2-(3-formylbiphenyl-4-yl)-6-phenylnapthalene was added dropwise, followed by stirring at room temperature for 17 hours. After the reaction, undissolved matters were filtered, and a filtrate was concentrated. Residues were purified by silica gel chromatography, whereby 330 g of 2-[3-(2-methoxy)ethenyl-1-yl]biphenyl-4-yl]-6-phenylnaphthalene (yield: 83%) was obtained.

(11-7) Synthesis of 2,8-diphenylchrysene 330 g (800 mmol) of 2-[3-(2-methoxy)ethenyl-1-yl]biphenyl-4-yl]-6-phenylnapthalene, 60 g (624 mmol) of methanesulfonic acid and 4.5 L of dehydrated dichloromethane were charged, and stirred at room temperature for 18 hours. Then, 1 L of methanol was added, and deposited crystals were filtered out. The resulting crystals were washed with methanol, whereby 240 g of 2,8-diphenylchrysene was obtained (yield: 78%).

(11-8) Synthesis of 6,12-dibromo-2,8-diphenylchrysene

In an argon atmosphere, 240 g (630 mmol) of 2,8-diphenylchrysene and 2.5 L of chloroform were charged in a flask. Then, 260 g of bromine was added dropwise, and the reaction solution was stirred for 45 hours at room temperature. The deposited crystals were filtered out, and washed with water and methanol. The resulting solids were repeatedly subjected to heating and washing with xylene, whereby 200 g of 6,12-dibromo-2,8-diphenylchrysene was obtained (yield: 59%).

(11-9) Synthesis of Compound 11

A compound was synthesized in substantially the same manner as in Example 1, except that 6,12-dibromo-2,8-diphenylchrysene was used instead of 6,12-dibromochrysene, and 4-(2-naphthyl)phenylboronic acid was used instead of 4-(1-naphthyl)phenylboronic acid. As a result of a mass spectroscopic analysis, the resulting compound was found to be an intended product, and had an m/e value of 784 relative to the molecular weight of 784.31.

Example 12

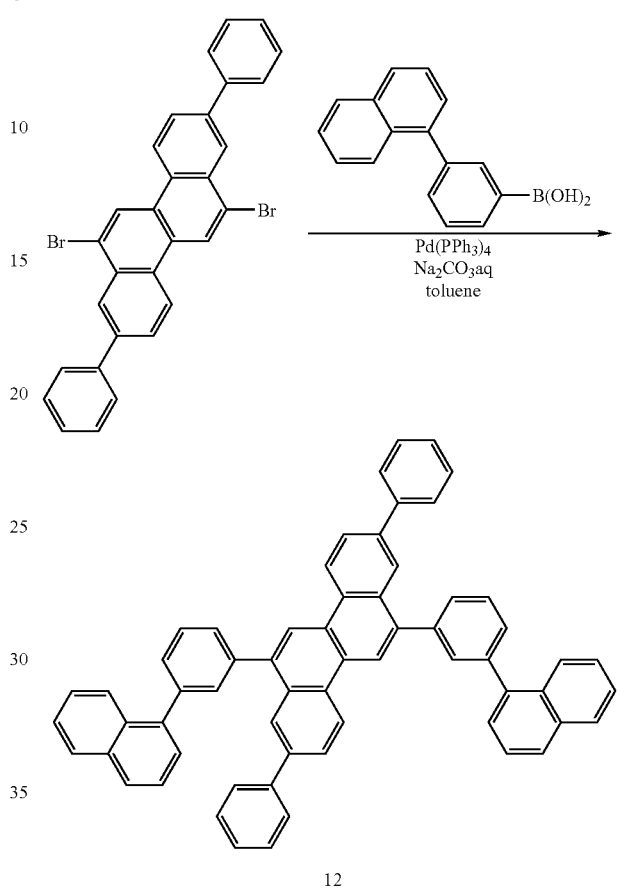

Synthesis of Compound 12

12

A compound was synthesized in substantially the same manner as in Example 1, except that 6,12-dibromo-2,8-diphenylchrysene was used instead of 6,12-dibromochrysene, and 3-(1-naphthyl)phenylboronic acid was used instead of 4-(1-naphthyl)phenylboronic acid. As a result of a mass spectroscopic analysis, the resulting compound was found to be an intended product, and had an m/e value of 784 relative to the molecular weight of 784.31.

Fabricating an Organic EL Device

Example 13

A glass substrate of 25 mm by 75 mm by 1.1 mm thick with an ITO transparent electrode (GEOMATEC CO., LTD.) was subjected to ultrasonic cleaning with isopropyl alcohol for 5 minutes, and cleaned with ultraviolet rays and ozone for 30 minutes.

The resultant substrate with transparent electrode lines was mounted on a substrate holder in a vacuum deposition device. First, the following compound A-1 was formed into a film in a thickness of 65 nm by resistant heat deposition so as to cover the surface of the transparent electrode on which the transparent electrode lines were formed. This A-1 film functioned as a hole-injecting/transporting layer.

Then, on the A-1 film, the compound 1 was formed into a film with a thickness of 40 nm by resistant heat deposition. Simultaneously, as a phosphorescent dopant, Ir(tpiq)2(acac)

(D-1) having the structure below was deposited such that the mass ratio thereof became 5% relative to the compound 1. This film functioned as the phosphorescent emitting layer.

Next, on this phosphorescent emitting layer, the following compound A-2 was formed into a film in a thickness of 10 nm by resistant heat deposition. This film of the compound A-2 functioned as a hole-blocking layer.

On this film, a tris(8-quinolinol)aluminum (Alq) complex was formed into a film in a thickness of 30 nm. This film functioned as an electron-transporting layer.

Then, Li as a reductive dopant (Li source: manufactured by SAES Getters Co., Ltd.) and Alq were co-deposited, whereby an Alq:Li film (film thickness: 0.5 nm) was formed as an electron-injecting layer.

Metal aluminum was deposited on the Alq:Li film to form a metallic cathode (film thickness: 150 nm), whereby an organic EL emitting device was fabricated.

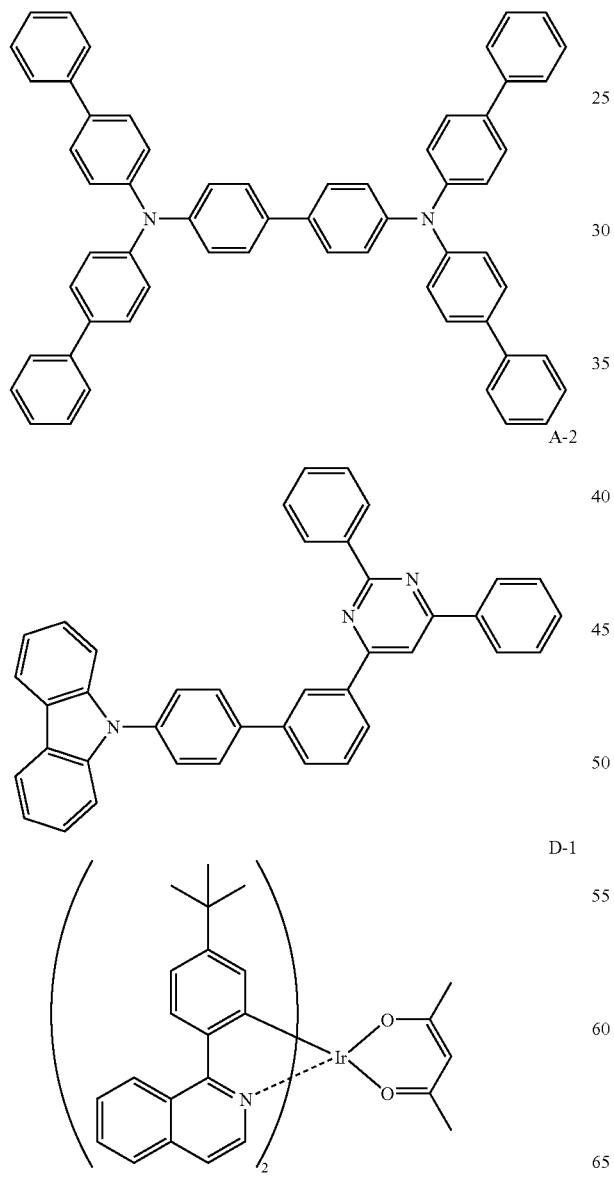

Examples 14 to Examples 24

An organic EL device was fabricated in substantially the same manner as in Example 1, except that compounds shown in Table 1 were used instead of the compound 1.

Comparative Example 1

An organic EL device was fabricated in substantially the same manner as in Example 1, except that the following compound A was used instead of the compound 1.

Compound A

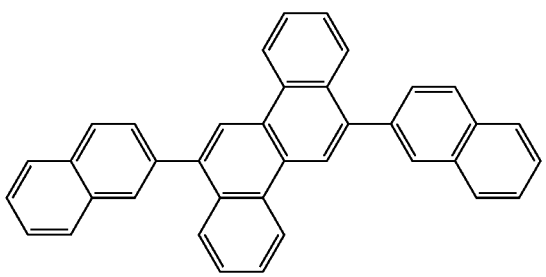

Comparative Example 2

An organic EL device was fabricated in substantially the same manner as in Example 1, except that the following compound B was used instead of the compound 1.

Compound B

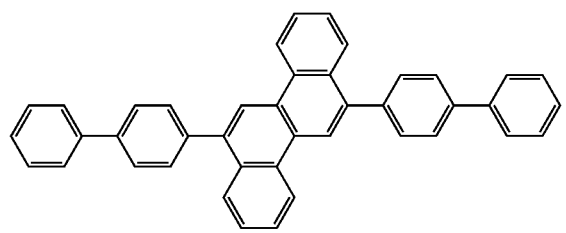

Comparative Example 3

An organic EL device was fabricated in substantially the same manner as in Example 1, except that the following compound C was used instead of the compound 1.

Compound C

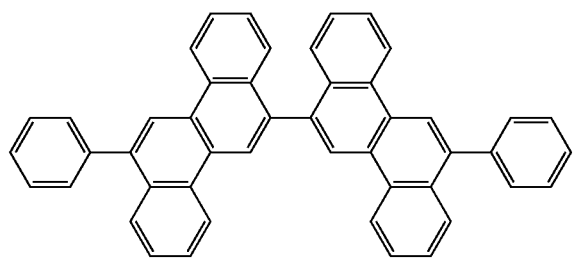

Comparative Example 4

An organic EL device was fabricated in substantially the same manner as in Example 1, except that the following compound D was used instead of the compound 1.

Compound D

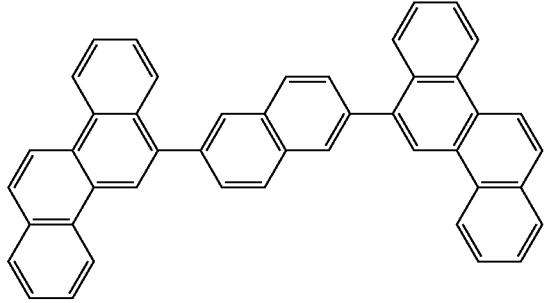

Comparative Example 5

An organic EL device was fabricated in substantially the same manner as in Example 1, except that the following compound E was used instead of the compound 1.
Compound E As for the organic EL devices fabricated in each of the above examples, the device

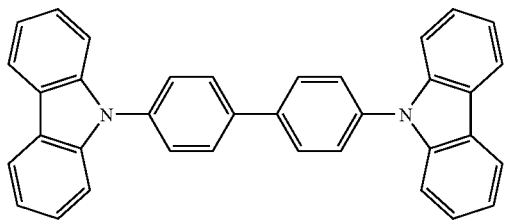

performance at the time of driving at 10 mA/cm² and the half life of an initial luminance of 1000 cd/m² were measured. The results are shown in Table 1.

As for the luminous efficiency, a prescribed voltage was applied to the device and the current value when the voltage was applied was measured, and a luminance was measured and calculated by means of a luminance meter (CS-1000, spectroradiometer manufactured by KONICA MINOLTA).

TABLE 1

| | Host material | Dopant material | Emission color | Voltage (V) | EQE (%) | Life-time (hr) |
|---|---|---|---|---|---|---|
| Example 13 | Compound 1 | D-1 | Red | 6.9 | 13.0 | 26000 |
| Example 14 | Compound 2 | D-1 | Red | 6.8 | 13.0 | 26000 |
| Example 15 | Compound 3 | D-1 | Red | 6.9 | 13.0 | 26000 |
| Example 16 | Compound 4 | D-1 | Red | 7.1 | 12.9 | 25000 |
| Example 17 | Compound 5 | D-1 | Red | 7.1 | 12.9 | 25000 |
| Example 18 | Compound 6 | D-1 | Red | 7.1 | 12.9 | 25000 |
| Example 19 | Compound 7 | D-1 | Red | 7.1 | 12.8 | 24000 |
| Example 20 | Compound 8 | D-1 | Red | 7.0 | 12.8 | 24000 |
| Example 21 | Compound 9 | D-1 | Red | 6.9 | 12.8 | 24000 |
| Example 22 | Compound 10 | D-1 | Red | 6.9 | 12.8 | 24000 |
| Example 23 | Compound 11 | D-1 | Red | 6.9 | 12.9 | 25000 |
| Example 24 | Compound 12 | D-1 | Red | 6.9 | 12.9 | 25000 |

TABLE 1-continued

| | Host material | Dopant material | Emission color | Voltage (V) | EQE (%) | Life-time (hr) |
|---|---|---|---|---|---|---|
| Com. Ex. 1 | Compound A | D-1 | Red | 7.9 | 10.4 | 15000 |
| Com. Ex. 2 | Compound B | D-1 | Red | 8.0 | 10.2 | 10000 |
| Com. Ex. 3 | Compound C | D-1 | Red | 8.1 | 10.3 | 10000 |
| Com. Ex. 4 | Compound D | D-1 | Red | 8.1 | 10.5 | 10000 |
| Com. Ex. 5 | Compound E | D-1 | Red | 6.5 | 10.2 | 3000 |

INDUSTRIAL APPLICABILITY

The chrysene derivative of the invention is preferable as a material for an organic EL device, in particular, as an emitting material.

The organic EL device of the invention can be suitably used as a light source such as a planar emitting body and backlight of a display, a display part of a portable phone, PDA, a car navigator, or an instrument panel of an automobile, an illuminator, and the like.

The contents of the above-described documents are herein incorporated by reference in its entirety.

Some embodiments and/or examples of the invention are explained above in detail. A person skilled in the art can add various modifications to these embodiments and/or examples, which are exemplification. Therefore, these various modifications are included in the scope of the invention.

The invention claimed is:
1. A chrysene derivative shown by the following formula (I):

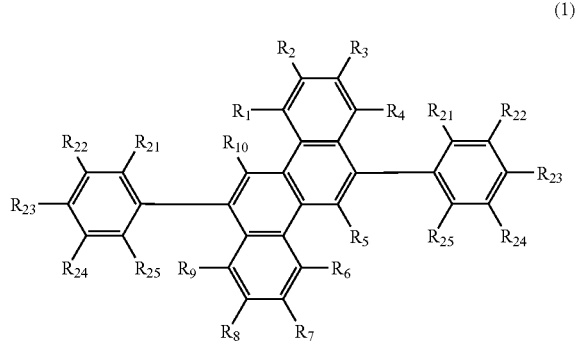

(1)

wherein $R_1$ to $R_{10}$ and $R_{21}$ to $R_{25}$ are independently a hydrogen atom, a substituted or unsubstituted alkyl group having 1 to 10 carbon atoms, a substituted or unsubstituted cycloalkyl group having 3 to 10 ring carbon atoms, a substituted or unsubstituted alkylsilyl group having 3 to 20 carbon atoms, a substituted or unsubstituted arylsilyl group having 8 to 30 carbon atoms, or a substituted or unsubstituted aryl group having 6 to 20 ring carbon atoms, provided that at least one of $R_{21}$ to $R_{25}$ is a substituted or unsubstituted fused aromatic ring group having 10 to 20 ring carbon atoms or a substituted or unsubstituted fluorenyl group.

2. The chrysene derivative according to claim 1, wherein $R_1$ to $R_{10}$ are a hydrogen atom.

3. The chrysene derivative according to claim 1, wherein one of $R_{21}$ to $R_{25}$ is a substituted or unsubstituted fused aromatic ring having 10 to 20 ring carbon atoms and the rest is a hydrogen atom.

4. The chrysene derivative according to claim 1, wherein one of $R_{21}$ to $R_{25}$ is a substituted or unsubstituted naphthyl group or a substituted or unsubstituted phenanthryl group and the rest is a hydrogen atom.

5. A material for an organic electroluminescence device comprising the chrysene derivative according to claim 1.

6. The material for an organic electroluminescence device according to claim 5 which is an emitting material.

7. An organic electroluminescence device comprising an anode, a cathode and one or more organic thin film layers including an emitting layer between the anode and the cathode, wherein at least one of the organic thin film layers comprises the material for an organic electroluminescence device according to claim 5.

8. The organic electroluminescence device according to claim 7, wherein the emitting layer comprises the material for an organic electroluminescence device.

9. The organic electroluminescence device according to claim 8, wherein the material for an organic electroluminescence device is a host material.

10. The organic electroluminescence device according to claim 7, wherein the emitting layer further comprises at least one of a fluorescent dopant and a phosphorescent dopant.

11. The organic electroluminescence device according to claim 10, wherein the phosphorescent dopant is a metal complex comprising at least one metal selected from the group of Ir, Pt, Os, Au, Cu, Re and Ru and a ligand.

12. The organic electroluminescence device according to claim 10, wherein the phosphorescent dopant exhibits an emission spectrum having a maximum peak wavelength at 520 nm to 700 nm.

13. The organic electroluminescence device according to claim 7, wherein the emitting layer further comprises a phosphorescent dopant.

* * * * *